(12) United States Patent
Kawakami et al.

(10) Patent No.: US 12,042,550 B2
(45) Date of Patent: Jul. 23, 2024

(54) LEAVE-ON HAIR TREATMENT COMPOSITIONS

(71) Applicant: L'OREAL, Paris (FR)

(72) Inventors: Kazumitsu Kawakami, Westfield, NJ (US); Shui Zou, Shanghai (CN); Aakash Jagat Parekh, Edison, NJ (US); Liliana Xavier, Mountainside, NJ (US); Olivia Isard, Tokyo (JP)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/936,440

(22) Filed: Sep. 29, 2022

(65) Prior Publication Data

US 2024/0122821 A1    Apr. 18, 2024

(51) Int. Cl.
| | | |
|---|---|---|
| *A61K 8/06* | (2006.01) | |
| *A61K 8/31* | (2006.01) | |
| *A61K 8/34* | (2006.01) | |
| *A61K 8/37* | (2006.01) | |
| *A61K 8/39* | (2006.01) | |
| *A61K 8/81* | (2006.01) | |
| *A61K 8/891* | (2006.01) | |
| *A61Q 5/00* | (2006.01) | |
| *A61Q 5/06* | (2006.01) | |
| *A61Q 5/12* | (2006.01) | |

(52) U.S. Cl.
CPC .............. *A61K 8/064* (2013.01); *A61K 8/31* (2013.01); *A61K 8/34* (2013.01); *A61K 8/375* (2013.01); *A61K 8/39* (2013.01); *A61K 8/8111* (2013.01); *A61K 8/891* (2013.01); *A61Q 5/002* (2013.01); *A61Q 5/06* (2013.01); *A61Q 5/12* (2013.01); *A61K 2800/30* (2013.01); *A61K 2800/48* (2013.01)

(58) Field of Classification Search
CPC ............ A61K 8/064; A61K 8/31; A61K 8/34; A61K 8/375; A61K 8/39; A61K 8/8111; A61K 8/891; A61K 2800/30; A61K 2800/48; A61Q 5/002; A61Q 5/06; A61Q 5/12
USPC ........................................................ 424/73
See application file for complete search history.

(56) References Cited

U.S. PATENT DOCUMENTS

| | | | |
|---|---|---|---|
| 6,602,494 B1 | 8/2003 | Jahedshoar et al. | |
| 8,562,957 B2 | 10/2013 | Kokeguchi et al. | |
| 2004/0234491 A1* | 11/2004 | Brautigam | A61K 8/8152 |
| | | | 424/70.28 |
| 2006/0292106 A1 | 12/2006 | Fares et al. | |
| 2007/0196300 A1 | 8/2007 | Johns et al. | |
| 2009/0070945 A1 | 3/2009 | Nguyen et al. | |
| 2009/0071493 A1 | 3/2009 | Nguyen et al. | |
| 2009/0071494 A1 | 3/2009 | Nguyen et al. | |
| 2009/0071495 A1 | 3/2009 | Nguyen et al. | |
| 2009/0074683 A1 | 3/2009 | Nguyen et al. | |
| 2009/0074700 A1 | 3/2009 | Nguyen et al. | |
| 2010/0322876 A1 | 12/2010 | Nguyen et al. | |
| 2012/0279514 A1* | 11/2012 | Ricard | A61K 8/062 |
| | | | 132/200 |
| 2013/0272976 A1 | 10/2013 | Nguyen et al. | |
| 2013/0272981 A1 | 10/2013 | Nguyen et al. | |
| 2013/0302385 A1 | 11/2013 | Muenz et al. | |
| 2014/0105942 A1 | 4/2014 | Pistorio et al. | |
| 2015/0290109 A1 | 10/2015 | Simonnet et al. | |
| 2016/0346172 A1 | 12/2016 | Pistorio et al. | |
| 2020/0405618 A1 | 12/2020 | Kadish et al. | |
| 2021/0059922 A1 | 3/2021 | Ghani et al. | |
| 2021/0113451 A1 | 4/2021 | Zarket et al. | |
| 2021/0186848 A1 | 6/2021 | Chen | |
| 2021/0267871 A1 | 9/2021 | Parikh | |
| 2022/0096345 A1 | 3/2022 | Chiou et al. | |

FOREIGN PATENT DOCUMENTS

| | | | | |
|---|---|---|---|---|
| CN | 106562914 | A | 4/2017 | |
| CN | 111150668 | A | 5/2020 | |
| EP | 2090295 | B2 | 8/2018 | |
| EP | 2392314 | B1 | 8/2019 | |
| EP | 3496700 | B1 | 8/2020 | |
| FR | 3115203 | A1 | 4/2022 | |
| KR | 20130050553 | A | 5/2013 | |
| WO | WO-2015099198 | A1 * | 7/2015 | ............. A61K 8/062 |

OTHER PUBLICATIONS

Schmidt, Allison. "Hairspray and Gel: When to Use What in Your Hair Styling Routine." Feb. 13, 2020. All Things Hair. https://www.allthingshair.com/en-us/hair-products/hair-gel/hairspray-or-gel-on-hair/ (Year: 2020).*

Preliminary Search Report and Written Opinion issued on Jun. 14, 2023 for corresponding French Application No. FR 2212546.

Datbase GNPD [Online]; Mintel; Anonymous: "Leave-In Serum," 2023 XP093053951.

* cited by examiner

*Primary Examiner* — Frederick F Krass
*Assistant Examiner* — Lucy M Tien
(74) *Attorney, Agent, or Firm* — POLSINELLI PC

(57) ABSTRACT

In the instant disclosure relates to a leave-on hair treatment composition and to methods for treating hair using the hair treatment composition. The hair treatment composition include: (a) water; (b) about 5 to about 40 wt. % of one or more polyols chosen from glycerin, ethylene glycol, propylene glycol, butylene glycol, hexylene glycol, pentylene glycol, diethylene glycol, dipropylene glycol, 1,3 propanediol, and a mixture thereof; (c) at least 20 wt. % of one or more oils; and (d) at least 0.5% of one or more C1-C9 non-polymeric and non-thiol, mono-, di-, and/or tri-carboxylic acids; and the ratio of ((a)+(b)) to (c) is about 1:1 to about 1:5. The composition imparts durability, hydration, and moisturization to hair in addition to desirable styling effects.

19 Claims, 7 Drawing Sheets

LEAVE-ON HAIR TREATMENT COMPOSITIONS

FIELD OF THE DISCLOSURE

The present disclosure relates to leave-on hair treatment compositions and methods for treating hair.

BACKGROUND

Many individuals suffer from dry, weak, and damaged hair. Dryness and damage can occur due to several factors including weather exposure, mechanical treatments (e.g. brushing hair), and chemical treatments (e.g., bleaching, etc.). Chemical treatments often change the look of hair by changing its physical structure, which inevitably causes a certain degree of damage to the hair. Environmental factors, such as salt water, sunlight, and heat, are also known to damage hair. Damaged hair is characterized by unnatural changes to the protein structure of the individual hair strands or shafts. Damage results in split ends, dry straw-like hair, hair that is easily broken, and hair that is "frizzy" and unmanageable. Because the visible portion of hair is dead, it cannot regenerate itself. Numerous over the counter and salon treatments purport to repair damaged hair. These include conditioners, hot oil hydrolyzed proteins, vitamin formulations, and exotic fruit, leaf, or root extracts. Such treatments, however, provide only limited improvements to the hair. Therefore, hair repair and conditioning technologies that restore the properties of hair to its natural form are needed.

SUMMARY OF THE DISCLOSURE

The leave-on hair-treatment compositions and methods of the instant disclosure provide a variety of benefits to hair. For example, the compositions and methods strengthen the hair fiber, protect hair fibers from damage (or from further damage), and improve cosmetic attributes such as softness, conditioning, and healthy appearance. The compositions include an unusually high amount of oil, yet are stable, translucent, or transparent, with a unique gel-like consistency. The compositions strengthen hair and moisturize/hydrate the hair without greasiness despite containing the very high amount of oil. The leave-on hair-treatment composition includes:
  (a) water;
  (b) about 5 to about 40 wt. % of one or more polyols selected from glycerin, ethylene glycol, propylene glycol, butylene glycol, hexylene glycol, pentylene glycol, diethylene glycol, dipropylene glycol, 1,3 propanediol, and a mixture thereof;
  (c) at least 20 wt. % of one or more oils; and
  (d) at least 0.5% of one or more C1-C9 non-polymeric and non-thiol, mono-, di-, and/or tri-carboxylic acids;
    wherein the ratio of ((a)+(b)) to (c) is about 1:1 to about 1:5; and
    all percentages by weight are relative to a total weight of the composition.

Preferably, the composition is transparent or translucent. In addition, the composition preferably has a pH of about 3 to about 6.

In various embodiments, at least one of the one or more oils is a hydrocarbon-based oil. In various embodiments, at least one of the one or more oils is a silicone-based oil (or simply a "silicone oil"). In further embodiments, the leave on hair treatment composition includes one or more hydrocarbon-based oil and one or more silicone-based oils. The oils may be volatile or non-volatile and may be of animal, plant, mineral, or synthetic origin.

Nonlimiting examples of hydrocarbon-based oils include those containing from 8 to 16 carbon atoms, and especially $C_8$-$C_{16}$ branched alkanes (also known as isoparaffins), for instance isododecane (also known as 2,2,4,4,6-pentamethylheptane), isodecane and isohexadecane, linear alkanes, and mixtures thereof. Nonlimiting examples of linear alkanes include n-nonane (C9), n-decane (C10), n-undecane (C11), n-dodecane (C12), n-tridecane (C13) and n-tetradecane (C14), and mixtures thereof.

Silicone-based oils can be volatile or non-volatile, and can be linear, branched, or cyclic. Nonlimiting examples include polydimethylsiloxane (dimethicone), dimethiconol, amodimethicone, phenyl-modified silicone, silicone block copolymers containing amine groups or quat groups or other charged or uncharged silicone block copolymers, and blends of any of the foregoing. Nonlimiting examples include octamethylcyclotetrasiloxane, decamethylcyclopentasiloxane, dodecamethylcyclohexa-siloxane, heptamethylhexyltrisiloxane, heptamethyl-octyltrisiloxane, hexamethyldisiloxane, octamethyltrisiloxane, decamethyltetrasiloxane and dodecamethylpentasiloxane, and mixtures thereof.

Nonlimiting examples of C1-C9 non-polymeric and no-thiol, mono-, di-, and tri-carboxylic acids include formic acid, acetic acid, lactic acid, propionic acid, butyric acid, gluconic acid, valeric acid, caproic acid, entanthic acid, caprylic acid, pelargonic acid, capric acid, undecylic acid, lauric acid, tridecylic acid, lauric acid, tridecylic acid, myristic acid, pentadecylic acid, palmitic acid, margaric acid, stearic acid, nonadecylic acid, and arachidic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, and 2,6-naphthalene dicarboxylic acid, citric acid, isocitric acid, aconitric acid, propane-1,2,3-tricarboxylic acid, and benzene-1,3,5-tricarboxylic acid, a salt thereof, and a mixture thereof.

Nonlimiting example of monocarboxylic acids include acetic acid, lactic acid, propionic acid, butyric acid, gluconic acid, valeric acid, caproic acid, entanthic acid, caprylic acid, pelargonic acid, capric acid, undecylic acid, lauric acid, tridecylic acid, lauric acid, tridecylic acid, myristic acid, pentadecylic acid, palmitic acid, margaric acid, stearic acid, nonadecylic acid, and arachidic acid, a salt thereof, and a mixture thereof.

Nonlimiting examples of dicarboxylic acids include oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, and 2,6-naphthalene dicarboxylic acid, a salt thereof, and a mixture thereof.

Nonlimiting examples of tricarboxylic acids include citric acid, isocitric acid, aconitric acid, propane-1,2,3-tricarboxylic acid, and benzene-1,3,5-tricarboxylic acid, a salt thereof, and a mixture thereof. In a preferred embodiment, the leave-on hair treatment composition includes citric acid.

In various embodiments, the leave-on hair treatment composition includes one or more emulsifiers, for example, one or more emulsifier selected from non-silicone emulsifiers and silicone-based emulsifiers (or simply silicone emulsifiers). Nonlimiting examples of non-silicone emulsifiers include oxyalkylenated (more particularly polyoxyethylenated) fatty acid esters of glycerol; oxyalkylenated fatty acid esters of sorbitan; oxyalkylenated (oxyethylenated and/ or oxypropylenated) fatty acid esters; oxyalkylenated (oxyethylenated and/or oxypropylenated) fatty alcohol ethers; sugar esters such as sucrose stearate; oxyalkylenated (more particularly polyoxyethylenated) castor oil (for example PEG-60 hydrogenated castor oil); and combinations thereof.

Nonlimiting examples of silicone-based emulsifiers include PEG-10 dimethicone, PEG-12 dimethicone, PEG-14 dimethicone, PEG-17 dimethicone, PPG-12 dimethicone, PPG-17 dimethicone, and derivatized/functionalized forms thereof such as Bis-PEG/PPG-20/20 dimethicone bis-PEG/PPG-16/16 PEG/PPG-16/16 dimethicone, PEG/PPG-14/4 dimethicone, PEG/PPG-20/20 dimethicone, PEG/PPG-20/23 dimethicone, and perfluorononylethyl carboxydecyl PEG-10 dimethicone, and a combination thereof.

In various embodiments, the leave-on hair treatment composition includes one or more C1-C96 monoalcohols. Nonlimiting examples of monoalcohols having from 1 to 9 carbon atoms include methyl alcohol, ethyl alcohol, n-propyl alcohol, isopropyl alcohol, n-butyl alcohol, sec-butyl alcohol, isobutyl alcohol, t-butyl alcohol, n-pentyl alcohol, isopentyl alcohol, neopentyl alcohol, cyclopentyl alcohol, n-hexanol, cyclohexyl alcohol, and combination thereof.

In various embodiments, the leave-on hair treatment composition includes one or more thickening agents. Nonlimiting examples of thickening agents include polyacrylate crosspolymers including crosslinked polyacrylate polymers, cationic acrylate copolymers, anionic acrylic or carboxylic acid polymers, polyacrylamide polymers, polysaccharides, gums, polyquaterniums, vinylpyrrolidone homopolymers/copolymers, C8-24 hydroxyl substituted aliphatic acid, C8-24 conjugated aliphatic acid, sugar fatty esters, polyglyceryl esters, and a mixture thereof.

In various embodiments, the leave-on hair treatment composition includes one or more humectants, for example, one or more hydroxyalkyl ureas. Nonlimiting examples include N-(2-hydroxyethyl) urea, N-(2-hydroxypropyl) urea, N-(3-hydroxypropyl) urea, N-(2,3-dihydroxypropyl) urea, N-(2,3,4,5,6-pentahydroxyhexyl) urea, N-methyl-N-(1,3,4,5,6-pentahydroxy-2-hexyl) urea, N-methyl-N'-(1-hydroxy-2-methyl-2-propyl) urea, N-(1-hydroxy-2-methyl-2-propyl) urea, N-(1,3-dihydroxy-2-propyl) urea; N-(trishydroxymethyl) urea, N-ethyl-N'-(2-hydroxyethyl) urea, N,N-bis-(2-hydroxy-ethyl) urea, N,N'-bis-(2-hydroxyethyl) urea, N,N-bis-(2-hydroxypropyl) urea, N,N'-bis-(2-hydroxypropyl) urea, N,N-bis-(2-hydroxyethyl)-N'-propyl urea, N,N-bis-(2-hydroxypropyl)-N'-(2-hydroxyethyl) urea, N-tert-butyl-N'-(2-hydroxyethyl)-N'-(2-hydroxypropyl) urea, N-(1,3-dihydroxy-2-propyl)-N'-(2-hydroxyethyl) urea, N,N-bis-(2-hydroxyethyl)-N',N'-dimethyl urea, N,N,N',N'-tetrakis-(2-hydroxyethyl) urea, N',N'-bis-(2-hydroxyethyl)-N',N'-bis-(2-hydroxypropyl) urea. In a preferred embodiment, the leave-on hair treatment composition includes N-(2-hydroxyethyl) urea (hydroxyethyl urea).

The compositions of the instant disclosure are useful in methods for treating hair. For instance, the methods are particularly effective for imparting durability to hair, hydrating the hair, and moisturizing hair. The methods include applying a leave-on hair treatment composition according to the instant disclosure to hair, and optionally styling the hair. As the name indicates, the "leave-on" hair treatment composition remains on the hair.

Other subjects, characteristics, aspects, and advantages of embodiments of the disclosure will emerge even more clearly on reading the description and the various examples that follow.

BRIEF DESCRIPTION OF THE DRAWINGS

Implementations of the present technology will now be described, by way of example only, with reference to the attached figures, wherein.

Figure 1:
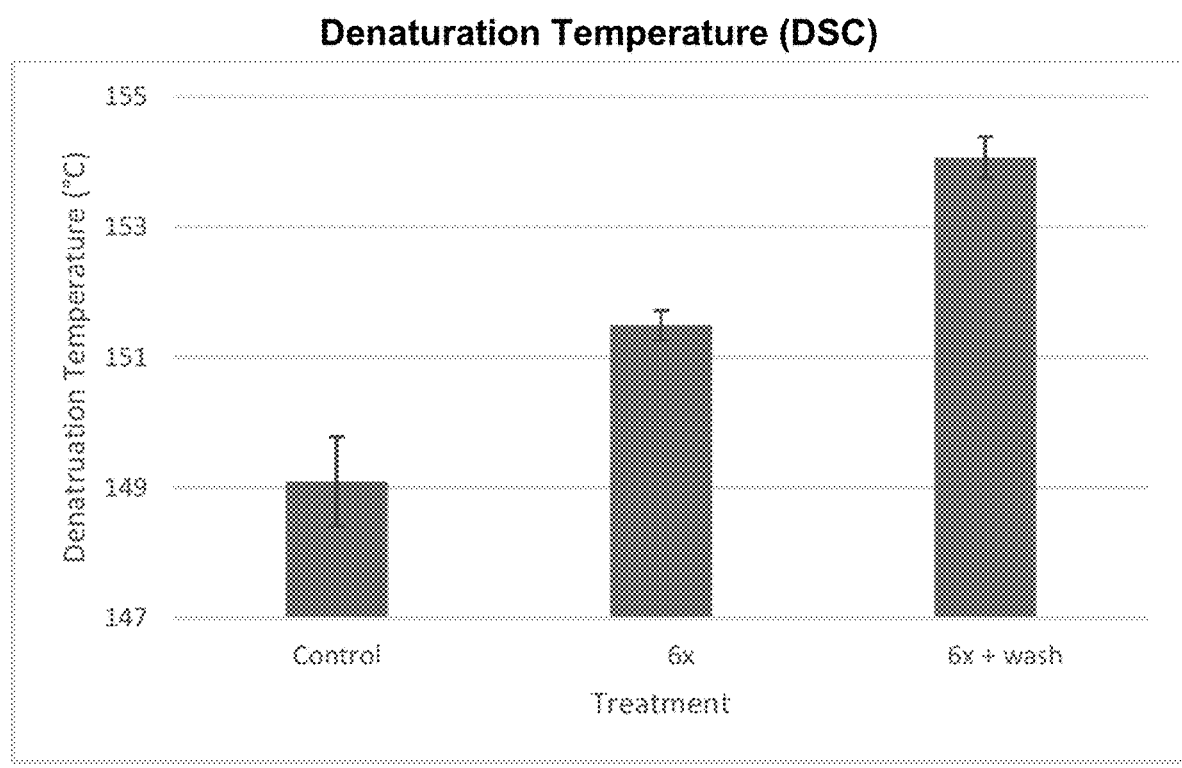
FIG. 1 is a graph showing the denaturization temperature (DSC) of a control, hair treated with a composition according to the instant disclosure, and hair treated with a composition of the instant disclosure and a shampoo.

It should be understood that the various aspects are not limited to the arrangements and instrumentality shown in the drawings.

DETAILED DESCRIPTION OF THE DISCLOSURE

The instant disclosure relates to leave-on hair treatment compositions and to methods for treating hair using the compositions. The compositions include a much higher than typical amount of oil, which helps to moisturize and hydrate the hair. Despite the inclusion of high amounts of oil, the compositions are surprisingly stable and transparent or translucent. Furthermore, the inventors found that the compositions surprisingly strengthen hair fibers, protect hair fibers from damage or further damage, and improve moisturization and hydration without imparting a greasiness to the hair.

The leave-on hair-treatment compositions include:
(a) water;
(b) about 5 to about 40 wt. % of one or more polyols selected from glycerin, ethylene glycol, propylene glycol, butylene glycol, hexylene glycol, pentylene glycol, diethylene glycol, dipropylene glycol, 1,3 propanediol, and a mixture thereof;
(c) at least 20 wt. % of one or more oils; and
(d) at least 0.5% of one or more C1-C9 non-polymeric and non-thiol, mono-, di-, and/or tri-carboxylic acids;
wherein the ratio of ((a)+(b)) to (c) is about 1:1 to about 1:5; and
all percentages by weight are relative to a total weight of the composition.

Preferably, the hair-treatment composition is transparent or translucent. In various embodiments, the hair-treatment composition is an emulsion, for example, a bicontinous emulsion. In further embodiments, the hair-treatment composition is a bicontinous microemulsion. Furthermore, in various embodiments, the hair-treatment composition is a bicontinous microemulsion gel.

(a) Water

The amount of water in the leave-on hair treatment composition will vary. In preferred embodiments, however, water is in an amount of about 5 to about 30 wt. %, based on the total weight of the leave-on hair treatment composition. In further embodiments, the leave-on hair treatment composition includes about 5 to about 25 wt. %, about 5 to about 20 wt. %, about 5 to about 15 wt. %, about 8 to about 30 wt. %, about 8 to about 25 wt. %, about 8 to about 20 wt. %, about 8 to about 15 wt. %, about 10 to about 30 wt. %, about 10 to about 25 wt. %, about 10 to about 20 wt. %, or about 10 to about 15 wt. %, based on the total weight of the leave-on hair treatment composition.

(b) Polyols

The leave-on hair treatment composition includes one or more poloyols, for example, glycerin and/or one or more glycols selected from ethylene glycol, propylene glycol, butylene glycol, hexylene glycol, pentylene glycol, diethylene glycol, dipropylene glycol, 1,3 propanediol, and a combination thereof. In a preferred embodiment, the leave-on hair treatment composition includes a combination of two or more polyols. For example, in various embodiments, the leave-on hair treatment composition includes glycerin and one or more additional polyols selected from ethylene glycol, propylene glycol, butylene glycol, hexylene glycol, pentylene glycol, diethylene glycol, dipropylene glycol, 1,3 propanediol, and a combination thereof.

The leave-on hair treatment composition preferably includes about 5 to about 40 wt. % of the one or more polyols, based on the total weight of the leave-on hair treatment composition. In further embodiments, the leave-on hair treatment composition includes about 5 to about 35 wt. %, about 5 to about 30 wt. %, about 5 to about 25 wt. %, about 5 to about 20 wt. %, about 8 to about 40 wt. %, about 8 to about 35 wt. %, about 8 to about 30 wt. %, about 8 to about 25 wt. %, about 8 to about 20 wt. %, about 10 to about 40 wt. %, about 10 to about 35 wt. %, about 10 to about 30 wt. %, about 10 to about 25 wt. %, about 10 to about 20 wt. %, about 15 to about 40 wt. %, about 15 to about 35 wt. %, about 15 to about 30 wt. %, or about 15 to about 25 wt. %, based on the total weight of the leave-on hair treatment composition.

In various embodiments, the leave on hair treatment composition includes about 1 to about 15 wt. % of glycerin and one or more additional polyols selected from ethylene glycol, propylene glycol, butylene glycol, hexylene glycol, pentylene glycol, diethylene glycol, dipropylene glycol, 1,3 propanediol, and a combination thereof. In further embodiments, the amount of glycerin is about 1 to about 12 wt. %, about 1 to about 10 wt. %, about 1 to about 8 wt. %, about 2 to about 15 wt. %, about 2 to about 12 wt. %, about 2 to about 10 wt. %, about 2 to about 8 wt. %, about 3 to about 15 wt. %, about 3 to about 12 wt. %, about 3 to about 10 wt. %, about 3 to about 8 wt. %, or about 4 to about 6 wt. %, based on the total weight of the leave-on hair treatment composition. As noted above, when glycerin is included in the leave-on hair treatment composition, one or more additional polyols can be included in the leave-on hair treatment compositions. The one or more additional polyols are preferably selected from ethylene glycol, propylene glycol, butylene glycol, hexylene glycol, pentylene glycol, diethylene glycol, dipropylene glycol, 1,3 propanediol, and a combination thereof. The one or more additional polyols are preferably in an amount of about 5 to about 35 wt. %, based on the total weight of the leave-on hair treatment composition. In further embodiments, the one or more additional polyols are in an amount of about 5 to about 30 wt. %, about 5 to about 20 wt. %, about 5 to about 15 wt. %, about 10 to about 35 wt. %, about 10 to about 30 wt. %, about 10 to about 25 wt. %, about 10 to about 20 wt. %, about 10 to about 15 wt. %, about 12 to about 35 wt. %, about 12 to about 30 wt. %, about 12 to about 25 wt. %, about 12 to about 20 wt. %, or about 12 to about 18 wt. %, based on the total amount of the leave-on hair treatment composition.

In various embodiments the leave-on hair treatment compositions includes glycerin and one or more additional poloyols (selected from ethylene glycol, propylene glycol, butylene glycol, hexylene glycol, pentylene glycol, diethylene glycol, dipropylene glycol, 1,3 propanediol, and a combination thereof) in a weight ratio of about 1:10 to about 1:1 (glycerin:additional polyol(s)). In further embodiments, the weight ratio is about 1:8 to about 1:1, about 1:6 to about 1:1, about 1:6 to about 1:1, about 1:5 to about 1:1, about 1:10 to about 1:1.5, about 1:8 to about 1:1.5, about 1:6 to about 1:1.5, about 1:5 to about 1:1.5, about 1:10 to about 1:2, about 1:8 to about 1:2, about 1:5 to about 1:2, or about 1:4 to about 1:2.

(c) Oils

The term "oil" means any fatty substance that is in liquid form at room temperature (20-25° C.) and at atmospheric pressure. The one or more oils can be hydrocarbon-based oils, silicone-based oils, fluoro oils, non-fluoro oils, or combinations thereof. The term "hydrocarbon-based oil" is interchangeable with the term "hydrocarbon oil." Also, the term "silicone-based oil" is interchangeable with the term "silicone oil." The one or more oils can be "volatile oils" or "non-volatile oils." For the purposes of the instant disclosure, the term "volatile oil" means an oil (or non-aqueous medium) capable of evaporating on contact with the skin in less than one hour, at room temperature and at atmospheric pressure. The volatile oil is a volatile cosmetic oil, which is liquid at room temperature, especially having a non-zero vapour pressure, at room temperature and atmospheric pressure, in particular having a vapour pressure ranging from 0.13 Pa to 40 000 Pa (10-3 to 300 mmHg), preferably ranging from 1.3 Pa to 13 000 Pa (0.01 to 100 mmHg), and preferentially ranging from 1.3 Pa to 1300 Pa (0.01 to 10 mmHg). Preferably, at least one of the one or more oils in the leave-on hair treatment compositions of the instant disclosure is a volatile oil. Furthermore, preferably the leave-on hair treatment compositions include at least one hydrocarbon-based oil and at least one silicone-based oil.

The amount of the one or more oils in the leave-on hair treatment compositions will vary. Nonetheless, in various embodiments, the leave-on hair treatment composition includes about 30 to about 70 wt. % of the one or more oils. Nonetheless, in further embodiments, the leave-on hair treatment composition includes about 30 to about 65 wt. %, about 30 to about 60 wt. %, about 30 to about 55 wt. %, about 35 to about 70 wt. %, about 35 to about 65 wt. %, about 35 to about 60 wt. %, about 35 to about 55 wt. %, about 40 to about 70 wt. %, about 40 to about 65 wt. %, about 40 to about 55 wt. %, about 45 to about 70 wt. %, about 45 to about 65 wt. %, about 45 to about 60 wt. %, about 45 to about 55 wt. %, about 50 to about 70 wt. %, about 50 to about 65 wt. %, or about 50 to bout 60 wt. %, based on the total weight of the leave-on hair treatment composition.

(c)(i) Hydrocarbon-Based Oil

In various embodiments, the leave-on hair treatment composition includes one or more hydrocarbon-based oils. The one or more hydrocarbon-based oils can be volatile or non-volatile hydrocarbon-based oils. In a preferred embodiment, at least one of the one or more hydrocarbon-based oils is a volatile hydrocarbon-based oil. Nonlimiting examples include the volatile hydrocarbon-based oils containing from 8 to 16 carbon atoms, and especially C8-C16 branched alkanes (also known as isoparaffins), for instance isododecane (also known as 2,2,4,4,6-pentamethylheptane), isodecane and isohexadecane, and for example the oils sold under the trade names ISOPAR® or PERMETHYL®, volatile linear alkanes, and mixtures thereof.

According to one advantageous embodiment, the volatile linear alkanes that are suitable for the invention have an evaporation rate ranging from 0.01 to 3.5 mg/cm2/min, at room temperature (25° C.) and atmospheric pressure (760 mmHg), and comprise from 9 to 14 carbon atoms. By way of example, mention may be made of n-nonane (C9), n-decane (C10), n-undecane (C11), n-dodecane (C12), n-tridecane (C13) and n-tetradecane (C14), and mixtures thereof. In various embodiments, at least one of the one or more hydrocarbon-based oils is a hydrocarbon based oil selected from C9-C12 alkane, C10-C13 alkane, alkane, C12-C17 alkane, C13-C15 alkane, C14-C17 alkane, C14-C19 alkane, C14-C20 alkane, C14-C22 alkane, C15-C19 alkane, C21-C28 alkane, C17-C23 alkane, C9-C12 isoalkane, C9-C13 isoalkane, C9-C14 isoalkane, C9-C16 isoalkane, C10-C11 isoalkane, C10-C12 isoalkane, C10-C13 isoalkane, isoalkane, C11-C13 isoalkane, C11-C14 isoalkane, C12-C14 isoalkane, C12-C20 isoalkane, C13-C14 isoalkane, C13-C16 isoalkane, C14-C16 isoalkane, C15-C19 isoalkane, isododecane, diethylhexylcyclohexane, undecane, tridecane, tetradecane, pentadecane, hexadecane, octadecane, docosane, squalane, hydrogenated polyisobutene, polybutene, hydrogenated polydecene, hydrogenated didecene, mineral oil, liquidum, petrolatum, dodecane, isohexadecane, isododecane, isoeicosane, and combinations thereof. In a preferred embodiment, at least one of the one or more oils is a hydrocarbon-based oil selected from isododecane and a C9-C16 isoalkane.

The total amount of the one or more hydrocarbon-based oils, if present, will vary. Nonetheless, in various embodiments, the total amount of the one or more hydrocarbon-based oil in the leave-on hair styling composition is about 20 to about 65 wt. %, based on the total weight of the leave-on hair styling composition. In further embodiments, the leave-on hair styling composition includes about 20 to about 60 wt. %, about 20 to about 55 wt. %, about 20 to about 50 wt. %, about 25 to about 65 wt. %, about 25 to about 60 wt. %, about 25 to about 55 wt. %, about 25 to about 50 wt. %, about 30 to about 65 wt. %, about 30 to about 60 wt. %, about 30 to about 50 wt. %, about 35 to about 65 wt. %, about 35 to about 60 wt. %, about 35 to about 55 wt. %, about 35 to about 50 wt. %, or about 40 to about 50 wt. %, based on the total weight of the leave-on hair treatment composition.

(c)(ii) Silicone-Based Oil

In various embodiments, the leave-on hair treatment composition includes one or more silicone-based oils. The one or more silicone-based oils can be volatile or non-volatile. In a preferred embodiment, at least one of the one or more silicone-based oils is a volatile silicone-based oil. Silicone-based oils include linear, branched, and cyclic silicone oils and include volatile and non-volatile silicone oils. Nonlimiting examples include polydimethylsiloxane (dimethicone), dimethiconol, amodimethicone, phenyl-modified silicone, silicone block copolymers containing amine groups or quat groups or other charged or uncharged silicone block copolymers, and blends of any of the foregoing. Additional nonlimiting examples include octamethylcyclotetrasiloxane, decamethylcyclopentasiloxane, dodecamethylcyclohexasiloxane, heptamethylhexyltrisiloxane, heptamethyl-octyltrisiloxane, hexamethyldisiloxane, octamethyltrisiloxane, decamethyltetrasiloxane and dodecamethylpentasiloxane, and mixtures thereof. In a preferred embodiment, the leave-on hair styling composition includes at least one silicone-based oil selected from dimethicone, dimethiconol, amodimethicone, and a combination thereof.

The total amount of the one or more silicone-based oils in the leave-on hair treatment composition, if present, will vary. Nonetheless, in various embodiments, the leave-on hair treatment composition includes about 1 to about 25 wt. % of one or more silicone-based oils. In further embodiments, the leave-on hair treatment composition includes about 1 to about 20 wt. %, about 1 to about 15 wt. %, about 2 to about 25 wt. %, about 2 to about 20 wt. %, about 2 to about 15 wt. %, about 5 to about 25 wt. %, about 5 to about 20 wt. %, about 5 to about 15 wt. %, about 8 to about 25 wt. %, about 8 to about 20 wt. %, about 8 to about 20 wt. %, or about 8 to about 15 wt. %, based on the total weight of the leave-on hair treatment composition.

As discussed above, the leave-on hair treatment compositions can include one or more hydrocarbon-based oil and one or more silicone-based oil. In various embodiments, the leave-on hair treatment compositions the weight ratio of the hydrocarbon-based oil to the silicone-based oil is about 10:1 to about 1:1 (hydrocarbon-based oil:silicone-based oil). In further embodiments, the weight ratio of the hydrocarbon-based oil to the silicone-based oil is about 8:1 to about 1:1, about 6:1 to about 1:1, about 5:1 to about 1:1, about 10:1 to about 2:1, about 8:1 to about 2:1, about 6:1 to about 2:1, about 5:1 to about 2:1, about 10:1 to about 3:1, about 8:1, about 3:1, about 6:1 to about 3:1, or about 5:1 to about 3:1.

As mentioned above, the one or more oils can be volatile or non-volatile. In various embodiments, the leave-on hair treatment compositions include one or more non-volatile oils. A nonlimiting list of non-volatile oils, silicone-based oils, etc. is provided later, under the heading "Oils."

The non-volatile oils can be hydrocarbon-based oils, silicone-based oils, fluoro oils, non-fluoro oils, or combinations thereof. The total amount of the one or more non-volatile oils, if present, will vary. Nonetheless, in various embodiments, the leave-on hair treatment composition includes about 0.01 to about 20 wt. % of the one or more non-volatile oils, based on the total weight of the leave-on hair treatment composition. In further embodiments, the leave-on hair treatment composition includes about 0.01 to about 15 wt. %, about 0.01 to about 10 wt. %, about 0.01 to about 5 wt. %, about 0.1 to about 15 wt. %, about 0.1 to about 10 wt. %, about 0.1 to about 5 wt. %, about 1 to about 15 wt. %, about 1 to about 10 wt. %, or about 1 to about 5 wt. %, based on the total weight of the leave-on hair treatment composition.

Ratio of ((a)+(b):(c)

The leave-on hair treatment compositions include a weight ratio of the water and the one or more polyols to the one or more oils of about 1:1 to about 1:5. However, in various embodiments, the weight ratio is about 1:1 to about 1:4.5, 1:1 to about 1:4, about 1:1.5 to about 5, about 1:1.5 to about 1:4.5, about 1:1.5 to about 4, about 1:2 to about 1:5, about 1:2 to about 1:45, about 1:2 to about 1:4, about 1:3 to about 5, about 1:3 to about 1:4.5, or about 1:3 to about 1:4.

(d) Non-Thiol, Mono-, Di-, and/or Tri-Carboxylic Acids

Nonlimiting examples of C1-C9 non-polymeric and non-thiol, mono-, di-, and tri-carboxylic acids include formic acid, acetic acid, lactic acid, propionic acid, butyric acid, gluconic acid, valeric acid, caproic acid, entanthic acid, caprylic acid, pelargonic acid, capric acid, undecylic acid, lauric acid, tridecylic acid, lauric acid, tridecylic acid, myristic acid, pentadecylic acid, palmitic acid, margaric acid, stearic acid, nonadecylic acid, and arachidic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, and 2,6-naphthalene dicarboxylic acid, citric acid, isocitric acid, aconitric acid, propane-1,2,3-tricarboxylic acid, and benzene-1,3,5-tricarboxylic acid, a salt thereof, and a mixture thereof. In various embodiments, the leave-on hair treatment composition comprises
- at least one monocarboxylic acid selected from formic acid, acetic acid, lactic acid, propionic acid, butyric acid, gluconic acid, valeric acid, caproic acid, entanthic acid, caprylic acid, pelargonic acid, capric acid, undecylic acid, lauric acid, tridecylic acid, lauric acid, tridecylic acid, myristic acid, pentadecylic acid, palmitic acid, margaric acid, stearic acid, nonadecylic acid, and arachidic acid, a salt thereof, and a mixture thereof;
- at least one dicarboxylic acid selected from oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, and 2,6-naphthalene dicarboxylic acid, a salt thereof, and a mixture thereof; and/or
- at least one tricarboxylic acid selected from citric acid, isocitric acid, aconitric acid, propane-1,2,3-tricarboxylic acid, and benzene-1,3,5-tricarboxylic acid, a salt thereof, and a mixture thereof. In a preferred embodiment, the leave-on hair treatment composition includes citric acid.

In a preferred embodiment, the leave-on hair treatment composition comprises citric acid. In further embodiments, the leave-on hair treatment composition comprises citric acid and optionally one or more additional C1-C9 non-polymeric and no-thiol, mono-, di-, and tri-carboxylic acids.

The total amount of the one or more C1-C9 non-polymeric and no-thiol, mono-, di-, and tri-carboxylic acids will vary. Nonetheless, the amount of the one or more C1-C9 non-polymeric and no-thiol, mono-, di-, and tri-carboxylic acids, salts thereof, or a combination thereof is preferably at least 0.5 wt. %, based on the total weight of the leave-on hair treatment composition. In various embodiments, the total amount of the one or more non-polymeric and no-thiol, mono-, di-, and tri-carboxylic acids, a salt thereof, or a combination thereof is at least 0.5 to about 5 wt. %, at least 0.5 to about 4 wt. %, at least 0.5 to about 3 wt. %, at least 0.5 to about 2 wt. %, about 0.8 to about 5 wt. %, about 0.8 to about 4 wt. %, about 0.8 to about 3 wt. %, about 0.8 to about 2 wt. %, about 1 to about 5 wt. %, about 1 to about 4 wt. %, about 1 to about 3 wt. %, or about 1 to about 2 wt. %, based on the total weight of the leave-on hair treatment composition.

(e) Emulsifiers

In various embodiments, the leave-on hair treatment composition includes one or more emulsifiers, for example, one or more emulsifiers selected from non-silicone emulsifiers and silicone-based emulsifiers (or simply silicone emulsifiers). Preferably, the one or more emulsifiers are nonionic emulsifiers. Furthermore, in a preferred embodiment, the leave-on hair treatment composition includes at least one non-silicone emulsifiers and at least one silicone-based emulsifier.

Nonlimiting examples of emulsifiers include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof. A more exhaustive but non-limiting list of useful nonionic emulsifiers is provided later, under the heading "Nonionic Emulsifiers."

The total amount of emulsifiers, if present, will vary. Nonetheless, in various embodiments, the leave-on hair treatment composition includes about 0.1 to about 10 wt. % of one or more emulsifiers, based on the total weight of the leave-on hair treatment composition. In further embodiments, the leave-on hair treatment composition includes about 0.1 to about 8 wt. %, about 0.1 to about 5 wt. %, about 0.1 to about 3 wt. %, about 0.5 to about 10 wt. %, about 0.5 to about 8 wt. %, about 0.5 to about 5 wt. %, about 0.5 to about 3 wt. %, about 1 to about 10 wt. %, about 1 to about 8 wt. %, about 1 to about 5 wt. %, or about 1 to about 3 wt. %, based on the total weight of the leave-on hair treatment composition.

(e)(i) Silicone-Based Emulsifiers

In various embodiments, the leave-on hair treatment composition includes one or more silicone-based emulsifiers. Nonlimiting examples include crosslinked organosiloxane emulsifiers such as dimethicone/dimethicone PEG/PPG 15 crosspolymer, dimethicone PEG-10 crosspolymer, dimethicone PEG-10/15 crosspolymer, dimethicone PEG-15 crosspolymer, dimethicone polyglycerin-3 crosspolymer, dimethicone PPG-20 crosspolymer, dimethiconol/methylsilanol/silicate crosspolymer; dimethiconol/silicate crosspolymer, lauryl dimethicone PEG-15 crosspolymer, lauryl dimethicone polyglycerin-3 crosspolymer, PEG-8 dimethicone polysorbate-20 crosspolymer, PEG-10 dimethicone/vinyl dimethicone crosspolymer, PEG-10 lauryl dimethicone crosspolymer, PEG-15/lauryl dimethicone crosspolymer, PEG-15 laurylpolydimethylsiloxyethyl crosspolymer, and combinations thereof. In various embodiments, the compositions include one or more linear organosiloxane emulsifier selected from the group consisting of cyclotetrasiloxane (and) cyclopentasiloxane (and) PEG/PPG-18 dimethicone, cyclopentasiloxane (and) PEG/PPG-18/18 dimethicone; PEG/PPG-18/18 dimethicone; lauryl PEG/PPG-18/18 methicone; cetyl PEG/PPG-14/14 dimethicone; bis-cetyl PEG/PPG-14/14 dimethicone; cetyl PEG/PPG-10/1 dimethicone; PEG-11 methyl ether dimethicone; PEG/PPG-20/22 butyl ether dimethicone; PEG-9 dimethicone; PEG-3 dimethicone; PEG-9 methyl ether dimethicone; PEG-10 dimethicone; lauryl PEG-9 polydimethylsiloxyethyl dimethicone, and a combination thereof.

In a preferred embodiment, the leave-on hair treatment composition includes one or more silicone-based emulsifiers selected from PEG-10 dimethicone, PEG-12 dimethicone, PEG-14 dimethicone, PEG-17 dimethicone, PPG-12 dimethicone, PPG-17 dimethicone, and derivatized/functionalized forms thereof such as Bis-PEG/PPG-20/20 dimethicone bis-PEG/PPG-16/16 PEG/PPG-16/16 dimethicone, PEG/PPG-14/4 dimethicone, PEG/PPG-20/20 dimethicone, PEG/PPG-20/23 dimethicone, and perfluorononylethyl carboxydecyl PEG-10 dimethicone, and a combination thereof.

A more exhaustive but nonlimiting list of silicone-based emulsifiers is provided later, under the heading "emulsifiers."

The amount of the one or more silicone-based emulsifiers in the leave-on hair treatment composition, if present, will vary. Nonetheless, in various embodiments, the leave-on hair treatment composition includes about 0.1 to about 9 wt. % of the one or more silicone-based emulsifiers, based on the total weight of the leave-on hair treatment composition. In further embodiments, the leave-on hair treatment composition includes about 0.1 to about 8 wt. %, about 0.1 to about 5 wt. %, about 0.1 to about 3 wt. %, about 0.5 to about 10 wt. %, about 0.5 to about 8 wt. %, about 0.5 to about 5 wt. %, about 0.5 to about 3 wt. %, about 1 to about 10 wt. %, about 1 to about 8 wt. %, about 1 to about 5 wt. %, or about 1 to about 3 wt. % of the one or more silicone-based emulsifers, based on the total weight of the leave-on hair treatment composition.

(e)(ii) Non-Silicone Emulsifiers

In various embodiments, the leave-on hair treatment composition includes one or more nonionic non-silicone emulsifers. Nonlimiting examples include oxyethylenated amides, oxyethylenated fatty alcohols, and block-copolymer (polycondensate) surfactants of ethylene oxide and of propylene oxide, and a mixture thereof. In a preferred embodiment, the hair coloring base composition includes PEG-4 rapeseedamide (an oxyethylenated amide), deceth-3 (an oxyethylenated fatty alcohol), poloxamer 338 (block-copolymer (polycondensate) surfactants of ethylene oxide and of propylene oxide), or a combination thereof.

Non-limiting examples of nonionic oxyethylenated amides are those of the following formula:

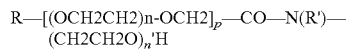

in which:
p denotes 0 or 1,
n denotes a number ranging from 1 to 10 and preferably from 1 to 6,
n' denotes a number ranging from 1 to 100 and preferably from 1 to 60,
R' denotes a hydrogen atom or a CH2CH2OH radical and preferably a hydrogen atom, and
R denotes a C10-C30 and preferably C12-C22 alkyl or alkenyl radical.

Examples of these compounds include AMIDET A15 sold by the company Kao (INCI name: Trideceth-2 carboxamide MEA), ETHOMID HP 60 sold by the company Akzo Nobel (INCI name: PEG-50 Hydrogenated Palmamide) and AMIDET N sold by the company Kao (INCI name: PEG-4 Rapeseedamide).

Non-limiting examples of fatty alcohols include saturated or unsaturated and linear or branched alcohols comprising from 6 to 30 carbon atoms and preferably from 8 to 30 carbon atoms, for instance, cetyl alcohol, isostearyl alcohol, stearyl alcohol and the mixture thereof (cetylstearyl alcohol), octyldodecanol, 2-butyloctanol, 2-hexyldecanol, 2-undecylpentadecanol, oleyl alcohol, linolenyl alcohol, ricinoleyl alcohol, undecylenyl alcohol and linoleyl alcohol, and mixtures thereof.

Non-limiting examples of oxyethylenated fatty alcohols include those comprising less than 10 OE units, preferably chosen from oxyethylenated derivatives of saturated or unsaturated, linear or branched, preferably linear, $C_8$-$C_{30}$ and preferably $C_{12}$-$C_{22}$ fatty alcohols, for instance cetyl alcohol, oleyl alcohol, oleocetyl alcohol, lauryl alcohol, behenyl alcohol, cetearyl alcohol, stearyl alcohol and isostearyl alcohol, and mixtures thereof.

As oxyethylenated fatty alcohols comprising less than 10 OE units, mention may be made of oxyethylenated fatty alcohols comprising from 2 to 8 and preferably from 2 to 6 OE units, for instance products of addition of ethylene oxide and lauryl alcohol, for instance lauryl alcohol 2 OE (CTFA name: laureth-2), products of addition of ethylene oxide and stearyl alcohol, for instance stearyl alcohol 2 OE (CTFA name: steareth-2), products of addition of ethylene oxide and decyl alcohol, for instance decyl alcohol 3 OE (CTFA name: deceth-3), decyl alcohol 5 OE (CTFA name: deceth-5), products of addition of ethylene oxide and oleocetyl alcohol, for instance oleocetyl alcohol 5 OE (CTFA name: oleoceteth-5), and mixtures thereof. In some instances, deceth-3 may be particularly useful.

Furthermore, non-limiting examples of oxyethylenated fatty alcohols having an average degree of ethoxylation of 2 to 29 are, for example, laureth-2, oleth-2, ceteareth-2, laneth-2, laureth-3, oleth-3, ceteareth-3, laureth-4, oleth-4, ceteareth-4, laneth-4, laureth-5, oleth-5, ceteareth-5, laneth-5, deceth-4, deceth-7, laureth-7, oleth-7, coceth-7, ceteth-7, ceteareth-7, C11-15 pareth-7, laureth-9, oleth-9, ceteareth-9, laureth-10, oleth-10, beheneth-10, ceteareth-10, laureth-12, ceteareth-12, trideceth-12, ceteth-15, laneth-15, ceteareth-15, laneth-16, ceteth-16, oleth-16, steareth-16, oleth-20, ceteth-20, ceteareth-20, laneth-20, steareth-21, ceteareth-23, ceteareth-25, ceteareth-27, and a mixture thereof.

Mention may be made, as block-copolymer (polycondensate) surfactant of ethylene oxide and of propylene oxide which may be used, of the polyethylene glycol/polypropylene glycol/polyethylene glycol triblock polycondensates sold under the "SYNPERONIC" names, such as "SYNPERONIC PE/F32" (INCI name: Poloxamer 108), "SYNPERONI. PE/F108" (INCI name: Poloxamer 338), "SYNPERONIC PE/L44" (INCI name: Poloxamer 124), "SYNPERONIC PE/L42" (INCI name: Poloxamer 122), "SYNPERONIC PE/F127" (INCI name: Poloxamer 407), "SYNPERONIC PE/F88" (INCI name: Poloxamer 238) or "SYNPERONIC PE/L64" (INCI name: Poloxamer 184), by Croda or also "LUTROL F68" (INCI name: Poloxamer 188), sold by BASF. In some instances, Poloxamer 338 may be particularly useful.

In various embodiments, the leave-on hair treatment composition includes one or more non-silicone emulsifiers. Nonlimiting examples include oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; oxyalkylenated (more particularly polyoxyethylenated) castor oil (for example PEG-60 hydrogenated castor oil); and combinations thereof. In a preferred embodiment, at least one of the one or more non-silicone emulsifiers is selected from PEG-7 glyceryl cocoate, PEG-20 methylglucoside sesquistearate, PEG-20 glyceryl tri-isostearate, PG-5 dioleate, PG-4 diisostearate, PG-10 isostearate, PEG-8 isostearate, and hydrogenated castor oil (for example, PEG-60 hydrogenated castor oil), and a combination thereof.

In various embodiments, the one or more non-silicone emulsifiers includes at least one oxyethylenated fatty alcohol, for example, those having an average degree of ethoxylation of 2 to 29 are, for example, laureth-2, oleth-2, ceteareth-2, laneth-2, laureth-3, oleth-3, ceteareth-3, laureth-4, oleth-4, ceteareth-4, laneth-4, laureth-5, oleth-5, ceteareth-5, laneth-5, deceth-4, deceth-7, laureth-7, oleth-7, coceth-7, ceteth-7, ceteareth-7, C11-15 pareth-7, laureth-9, oleth-9, ceteareth-9, laureth-10, oleth-10, beheneth-10, ceteareth-10, laureth-12, ceteareth-12, trideceth-12, ceteth-15, laneth-15, ceteareth-15, laneth-16, ceteth-16, oleth-16, steareth-16, oleth-20, ceteth-20, ceteareth-20, laneth-20, steareth-21, ceteareth-23, ceteareth-25, ceteareth-27, and a mixture thereof.

A more exhaustive list of useful non-silicone emulsifiers, including nonionic emulsifers that may be included in the reducing composition is provided later, under the heading "emulsifiers."

The total amount of the one or more non-silicone emulsifiers in the leave-on hair treatment composition, if present, will vary. Nonetheless, in various embodiments, the leave-on hair treatment composition includes about 0.01 to about 9 wt. % of one or more non-silicone emulsifiers, based on the total weight of the leave-on hair treatment composition. In further embodiments, the leave-on hair treatment composition includes about 0.01 to about 8 wt. %, about 0.01 to about 5 wt. %, about 0.01 to about 3 wt. %, about 0.1 to about 8 wt. %, about 0.1 to about 5 wt. %, about 0.1 to about 3 wt. %, about 0.5 to about 10 wt. %, about 0.5 to about 8 wt. %, about 0.5 to about 5 wt. %, or about 0.5 to about 3 wt. %, of the one or more non-silicone emulsifiers, based on the total weight of the leave-on hair treatment composition.

(f) Monoalcohols

In various embodiments, the leave-on hair treatment composition includes one or more C1-C9 monoalcohols, preferably one or more C1-C6 monoalcohols. Nonlimiting examples of monoalcohols having from 1 to 6 carbon atoms include methyl alcohol, ethyl alcohol, n-propyl alcohol, isopropyl alcohol, n-butyl alcohol, sec-butyl alcohol, isobutyl alcohol, t-butyl alcohol, n-pentyl alcohol, isopentyl alcohol, neopentyl alcohol, cyclopentyl alcohol, n-hexanol, cyclohexyl alcohol, and combination thereof. In a preferred embodiment, the leave-on hair treatment composition includes one or more monoalcohols selected from ethanol, isopropyl alcohol, and a mixture thereof. In another preferred embodiment, the leave-on hair treatment composition includes ethanol.

The amount of the one or more monoalcohols will vary. Nonetheless, in various embodiments, the leave-on hair treatment composition includes about 1 to about 20 wt. % of the one or more monoalcohols, based on the total weight of the leave-on hair treatment composition. In further embodiments, the leave-on hair treatment composition includes about 1 to about 15 wt. %, about 1 to about 12 wt. %, about 1 to about 10 wt. %, about 1 to about 8 wt. %, about 2 to about 20 wt. %, about 2 to about 15 wt. %, about 2 to about 12 wt. %, about 2 to about 10 wt. %, about 2 to about 8 wt. %, about 3 to about 15 wt. %, about 3 to about 12 wt. %, about 3 to about 10 wt. %, or about 3 to about 8 wt. %, based on the total weight of the leave-on hair treatment composition.

(g) Thickening Agents

In various embodiments, the leave-on hair treatment composition includes one or more thickening agents. Nonlimiting examples of thickening agents include polyacrylate crosspolymers including crosslinked polyacrylate polymers, cationic acrylate copolymers, polyacrylamides, anionic acrylic or carboxylic acid polymers, polyacrylamide polymers, polysaccharides, gums, polyquaterniums, vinylpyrrolidone homopolymers/copolymers, C8-24 hydroxyl substituted aliphatic acid, C8-24 conjugated aliphatic acid, sugar fatty esters, polyglyceryl esters, and a mixture thereof.

In various embodiments, the one or more thickening agents are preferably selected from: modified or unmodified carboxyvinyl polymers, such as the CARBOPOLS (CTFA name: carbomer); polyacrylates and polymethacrylates, such as the products sold under the names LUBRAJEL and NORGEL; polyacrylamides; polymers and copolymers of 2-acrylamido-2-methylpropanesulphonic acid, which are optionally crosslinked and/or neutralized, such as the poly (2-acrylamido-2-methylpropanesulphonic acid) sold under the name HOSTACERIN AMPS (CTFA name: ammonium polyacryldimethyltauramide); crosslinked anionic acrylamide/AMPS copolymers, such as those sold under the name SEPIGEL 305 (CTFA name: Polyacrylamide/C13-14 Isoparaffin/Laureth-7) and under the name SIMULGEL 600 (CTFA name: Acrylamide/Sodium acryloyldimethyltaurate copolymer/Isohexadecane/Polysorbate 80); polysaccharide biopolymers, for instance xanthan gum, guar gum, carob gum, acacia gum, scleroglucans, chitin and chitosan derivatives, carrageenans, gellans, alginates, celluloses such as microcrystalline cellulose, carboxymethyl cellulose, hydroxymethyl cellulose and hydroxypropyl cellulose; and mixtures thereof. In a preferred embodiment, the one or more thickening agents are selected from polymeric thickening agents. In a further preferred embodiment, at least one of the one or more thickening agents is a polyacrylamide.

The total amount of the one or more thickening agents, if present, will vary. Nonetheless, in various embodiments, the leave-on hair treatment composition includes about 0.01 to about 6 wt. % of the one or more thickening agents, based on the total weight of the leave-on hair treatment composition. In further embodiments, the leave-on hair treatment composition includes about 0.01 to about 5 wt. %, about 0.01 to about 3 wt. %, about 0.01 to about 2 wt. %, about 0.05 to about 5 wt. %, about 0.05 to about 3 wt. %, about 0.05 to about 2 wt. %, about 0.1 to about 5 wt. %, about 0.1 to about 3 wt. %, about 0.1 to about 2 wt. %, about 0.5 to about 5 wt. %, about 0.5 to about 3 wt. %, or about 0.5 to about 2 wt. % of the one or more thickening agents, based on the total weight of the leave-on hair treatment composition.

(h) Humectant (Moisturizing Agent)

In various embodiments, the leave-on hair treatment composition includes one or more humectants. Non-limiting examples of humectants include hydroxyalkyl ureas (such as hydroxyethyl urea), amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol. Additional nonlimiting examples include acetylated lanolin, acetylated lanolin alcohol, alanine, algae extract, *Aloe barbadensis*, *Aloe-barbadensis* extract, *Aloe barbadensis* gel, *Althea officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamon (*Elettaria cardamomum*) oil, carnauba (Copernicia cerifera)

wax, carrot (*Daucus carota sativa*) oil, castor (*Ricinus communis*) oil, ceramides, ceresin, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *Eucalyptus globulus* oil, evening primrose (*Oenothera biennis*) oil, fatty acids, *Geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (Carthamus tinctorius) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica* limonum) oil, linoleic acid, linolenic acid, *Macadamia ternifolia* nut oil, maltitol, matricaria (*Chamomilla recutita*) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (Citrus aurantium *dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, pentadecalactone, peppermint (*Mentha piperita*) oil, petrolatum, phospholipids, polyamino sugar condensate, polyglyceryl-3 diisostearate, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (Carthamus tinctorius) oil, sage (*Salvia officinalis*) oil, sandalwood (Santalum album) oil, serine, serum protein, sesame (*Sesamum indicum*) oil, shea butter (Butyrospermum parkii), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil, and a combination there.

In various embodiment, the leave-on hair treatment compositions include at least on hydroxyalkyl urea. Nonlimiting examples include N-(2-hydroxyethyl) urea, N-(2-hydroxypropyl) urea, N-(3-hydroxypropyl) urea, N-(2,3-dihydroxypropyl) urea, N-(2,3,4,5,6-pentahydroxyhexyl) urea, N-methyl-N-(1,3,4,5,6-pentahydroxy-2-hexyl) urea, N-methyl-N'-(1-hydroxy-2-methyl-2-propyl) urea, N-(1-hydroxy-2-methyl-2-propyl) urea, N-(1,3-dihydroxy-2-propyl) urea; N-(trishydroxymethylmethyl) urea, N-ethyl-N'-(2-hydroxyethyl) urea, N,N-bis-(2-hydroxy-ethyl) urea, N,N'-bis-(2-hydroxyethyl) urea, N,N-bis-(2-hydroxypropyl) urea, N,N'-bis-(2-hydroxypropyl) urea, N,N-bis-(2-hydroxyethyl)-N'-propyl urea, N,N-bis-(2-hydroxypropyl)-N'-(2-hydroxyethyl) urea, N-tert-butyl-N'-(2-hydroxyethyl)-N'-(2-hydroxypropyl) urea, N-(1,3-dihydroxy-2-propyl)-N'-(2-hydroxyethyl) urea, N,N-bis-(2-hydroxyethyl)-N',N'-dimethyl urea, N,N,N',N'-tetrakis-(2-hydroxyethyl) urea, N',N'-bis-(2-hydroxyethyl)-N',N'-bis-(2-hydroxypropyl) urea. In a preferred embodiment, the leave-on hair treatment composition includes N-(2-hydroxyethyl) urea (hydroxyethyl urea).

The total amount of the one or more humectants, if present, will vary. Nonetheless, in various embodiments, the leave-on hair treatment composition includes about 0.1 to about 10 wt. % of the one or more humectants, based on the total weight of the leave-on hair treatment composition. In further embodiments, the leave-on hair treatment composition includes about 0.1 to about 8 wt. %, about 0.1 to about 5 wt. %, about 0.1 to about 4 wt. %, about 0.5 to about 10 wt. %, about 0.5 to about 8 wt. %, about 0.5 to about 5 wt. %, about 0.5 to about 4 wt. %, about 1 to about 10 wt. %, about 1 to about 8 wt. %, about 1 to about 5 wt. %, or about 1 to about 4 wt. %, based on the total weight of the leave-on hair treatment composition.

(i) Miscellaneous Ingredients

In various embodiments, the leave-on hair treatment composition includes one or more miscellaneous ingredients. Miscellaneous ingredients are ingredients that are compatible with the leave-on hair treatment composition and do not disrupt or materially affect the basic and novel properties of the leave-on hair treatment compositions. Nonlimiting examples of ingredients include preservatives, fragrances, pH adjusters, salts, chelating agents, buffers, antioxidants, flavonoids, vitamins, botanical extracts, UV filtering agents, proteins, protein hydrolysates, and/or isolates, fillers, composition colorants, cationic polymers, fatty compounds that are not oils (fatty compounds that are solid at room temperature), etc.

For purposes of the instant disclosure fatty compounds that are not oils are fatty compounds that are solid at room temperature. Nonlimiting examples include waxes, fatty acids and fatty alcohols that are solid at room temperature, and the like. The leave-on hair treatment compositions of the instant disclosure optionally include one or more fatty compounds that are not oils (one or more fatty compounds that are solid at room temperature). Although the fatty compounds are solid at room temperature, when combined with other components, for example, when combined in the hair-treatment compositions of the instant disclosure, the compounds are not generally solid because they solubilize or interact with the other compounds in the composition.

For purposes of the instant disclosure, a "composition colorant" is a compound that colors the composition but does not have an appreciable coloring effect on hair. In other words, the composition colorant is included to provide a coloring to the composition for aesthetic appeal, which is not intended to impart coloring properties to hair. Styling gels, for example, can be found in a variety of different colors (e.g., light blue, light pink, etc.) yet application of the styling gel to the hair does not change the color of the hair.

In various embodiments, preferred miscellaneous ingredients are chosen from preservatives, fragrances, pH adjusters, salts, chelating agents, buffers, composition colorants, fatty compounds that are not oils (solid fatty compounds), and mixtures thereof.

The total amount of the one or more miscellaneous ingredients, if present, will vary. Nonetheless, in various embodiments, reducing composition includes about 0.001 to about 10 wt. % of one or more miscellaneous ingredients, based on the total weight of the reducing composition. In further embodiments, the reducing compositions include from about 0.001 to about 5 wt. %, about 0.001 to about 3 wt. %, about 0.01 to about 10 wt. %, about 0.01 to about 5 wt. %, about 0.01 to about 3 wt. %, about 0.1 to about 10 wt. %, about 0.1 to about 5 wt. %, or about 0.1 to about 3 wt. % of one or more miscellaneous ingredients, based on the total weight of the reducing composition.

pH

The pH of the leave-on hair treatment compositions will vary. Nonetheless, in various embodiments, the pH of the composition is from about 3 to about 6. In further embodiments, the pH of the compositions is from about 3 to about 5.5, about 3 to about 5, about 3 to about 4.5, about 3 to about 4, about 3.5 to about 6, about 3.5 to about 5.5, about 3.5 to about 5, about 3.5 to about 4.5, about 4 to about 6, about 4 to about 5.5, or about 4 to about 5.

The compositions of the instant disclosure are useful in methods for treating hair. For instance, the methods are particularly effective for imparting durability to hair, hydrating the hair, and moisturizing hair. The methods include applying a leave-on hair treatment composition according to the instant disclosure to hair, and optionally styling the hair. As the name indicates, the "leave-on" hair treatment composition remains on the hair.

Viscosity

The viscosity of the leave-on hair treatment compositions will vary. Nonetheless, it is preferable if the viscosity is from about 100 to 20,000 cps at 25° C. measured with a Brookfield DV-LL+ Pro Viscometer using Helipath T-Bar Spindle C and rotational speed of 50% RPM. In further embodiments, the viscosity is from about 100 to about 15,000 cps, about 100 to about 10,000 cps, about 100 to about 5,000 cops, about 500 to about 20,000 cps, about 500 to about 15,000 cps, about 500 to about 10,000 cps, about 500 to about 5,000 cps, about 1,000 to about 20,000 cps, about 1,000 to about 15,000 cps, about 1,000 to about 10,000 cps, about 1,000 to about 5,000 cps, about 5,000 to about 20,000 cps, about 5,000 to about 15,000 cps, about 5,000 to about 10,000 cps, about 10,000 to about 20,000 cps, about 10,000 to about 15,000 cps, or about 15,000 to about 20,000 cps at 25° C. measured with a Brookfield DV-LL+ Pro Viscometer using Helipath T-Bar Spindle C and rotational speed of 50% RPM.

Preferred Embodiments

In various embodiments, the leave-on hair treatment composition comprises or consists of:
  (a) about 5 to about 30 wt. %, preferably about 5 to about 25 wt. %, more preferably about 5 to about 20 wt. % of water;
  (b) about 10 to about 40 wt. %, more preferably about 10 to about 30 wt. %, more preferably about 15 to about 25 wt. % of one or more polyols chosen from glycerin, ethylene glycol, propylene glycol, butylene glycol, hexylene glycol, pentylene glycol, diethylene glycol, dipropylene glycol, 1,3 propanediol, and a mixture thereof, preferably glycerin and one or more additional polyols chosen from ethylene glycol, propylene glycol, butylene glycol, hexylene glycol, pentylene glycol, diethylene glycol, dipropylene glycol, 1,3 propanediol, and a mixture thereof, more preferably glycerin and dipropylene glycol;
  (c) about 35 to about 75 wt. % of one or more oils, preferably about 40 to about 70 wt. %, more preferably about 45 to about 65 wt. % of one or more oil, preferably at least one hydrocarbon-based oil and at least one silicone-based oil; more preferably wherein the one or more oils comprise:
    (c)(i) about 30 to about 60 wt. %, preferably about 35 to about 55 wt. %, more preferably about 35 to about 50 wt. % of one or more hydrocarbon-based oils; and
    (c)(ii) about 1 to about 25 wt. %, preferably about 5 to about 25 wt. %, more preferably about 5 to about 20 wt. % of one or more silicone-based oils;
  (d) at least 0.5% to about 5 wt. %, preferably at least 0.5 to about 3 wt. %, more preferably about 0.8 to about 3 wt. % of one or more C1-C9 non-polymeric and non-thiol, mono-, di-, and/or tri-carboxylic acids, a salt thereof, or a combination thereof, preferably selected from formic acid, acetic acid, lactic acid, propionic acid, butyric acid, gluconic acid, valeric acid, caproic acid, entanthic acid, caprylic acid, pelargonic acid, capric acid, undecylic acid, lauric acid, tridecylic acid, lauric acid, tridecylic acid, myristic acid, pentadecylic acid, palmitic acid, margaric acid, stearic acid, nonadecylic acid, and arachidic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, and 2,6-naphthalene dicarboxylic acid, citric acid, isocitric acid, aconitric acid, propane-1,2,3-tricarboxylic acid, and benzene-1,3,5-tricarboxylic acid, a salt thereof, and a combination thereof, more preferably citric acid and optionally one or more additional C1-C9 non-polymeric and non-thiol, mono-, di-, and/or tri-carboxylic acids, a salt thereof, or a combination thereof;
  (e) about 1 to about 10 wt. %, preferably about 1 to about 8, more preferably about 1 to about 5 wt. % of one or more emulsifiers, preferably one or more silicone-based emulsifiers and one or more non-silicone emulsifiers; (f) about 0.01 to about 5 wt. %, preferably about 0.1 to about 5 wt. %, more preferably about 0.5 to about 3 wt. % of one or more thickening agents, preferably one or more polymeric thickening agents, more preferably selected from polyacrylamides;

(g) optionally, up to about 5 wt. %, preferably about 0.1 to about 5 wt. %, more preferably about 0.5 to about 5 wt. %, more preferably about 1 to about 3 wt. % of one or more humectants, preferably wherein at least one or the one or more humectants is selected from hydroxyalkyl ureas, preferably one or more hydroxyethyl ureas selected from selected from N-(2-hydroxyethyl) urea, N-(2-hydroxypropyl) urea, N-(3-hydroxypropyl) urea, N-(2,3-dihydroxypropyl) urea, N-(2,3,4,5,6-pentahydroxyhexyl) urea, N-methyl-N-(1,3,4,5,6-pentahydroxy-2-hexyl) urea, N-methyl-N'-(1-hydroxy-2-methyl-2-propyl) urea, N-(1-hydroxy-2-methyl-2-propyl) urea, N-(1,3-dihydroxy-2-propyl) urea; N-(trishydroxymethylmethyl) urea, N-ethyl-N'-(2-hydroxyethyl) urea, N,N-bis-(2-hydroxy-ethyl) urea, N,N'-bis-(2-hydroxyethyl) urea, N,N-bis-(2-hydroxypropyl) urea, N,N'-bis-(2-hydroxypropyl) urea, N,N-bis-(2-hydroxyethyl)-N'-propyl urea, N,N-bis-(2-hydroxypropyl)-N'-(2-hydroxyethyl) urea, N-tert-butyl-N'-(2-hydroxyethyl)-N'-(2-hydroxypropyl) urea, N-(1,3-dihydroxy-2-propyl)-N'-(2-hydroxyethyl) urea, N,N-bis-(2-hydroxyethyl)-N',N'-dimethyl urea, N,N,N',N'-tetrakis-(2-hydroxyethyl) urea, N',N'-bis-(2-hydroxyethyl)-N',N'-bis-(2-hydroxypropyl) urea, more preferably hydroxyethyl urea; and (h) optionally, up to about 5 wt. %, preferably about 0.1 to about 5 wt. %, more preferably about 1 to about 5 wt. % of one or more miscellaneous ingredients;

wherein the ratio of ((a)+(b)) to (c) is 1:1 to 1:5, preferably about 1:2 to about 1:5, more preferably about 1:2 to about 1:4;

the composition is translucent or transparent; and the composition has a pH of about 3 to about 6.

all percentages by weight are relative to a total weight of the composition.

In various embodiments, the leave-on hair treatment composition comprises or consists of:

(a) about 5 to about 30 wt. %, preferably about 5 to about 25 wt. %, more preferably about 5 to about 20 wt. % of water;

(b) about 10 to about 40 wt. %, more preferably about 10 to about 30 wt. %, more preferably about 15 to about 25 wt. % of one or more polyols chosen from glycerin, ethylene glycol, propylene glycol, butylene glycol, hexylene glycol, pentylene glycol, diethylene glycol, dipropylene glycol, 1,3 propanediol, and a mixture thereof, preferably glycerin and one or more additional polyols chosen from ethylene glycol, propylene glycol, butylene glycol, hexylene glycol, pentylene glycol, diethylene glycol, dipropylene glycol, 1,3 propanediol, and a mixture thereof, more preferably glycerin and dipropylene glycol;

(c) about 35 to about 75 wt. % of one or more oils, preferably about 40 to about 70 wt. %, more preferably about 45 to about 65 wt. % of one or more oil, preferably at least one hydrocarbon-based oil and at least one silicone-based oil; more preferably wherein the one or more oils comprise:

(c)(i) about 30 to about 60 wt. %, preferably about 35 to about 55 wt. %, more preferably about 35 to about 50 wt. % of one or more hydrocarbon-based oils, preferably one or more hydrocarbon-based oils selected C9-C12 alkane, C10-C13 alkane, alkane, C12-C17 alkane, C13-C15 alkane, C14-C17 alkane, C14-C19 alkane, C14-C20 alkane, C14-C22 alkane, C15-C19 alkane, C21-C28 alkane, C17-C23 alkane, C9-C12 isoalkane, C9-C13 isoalkane, C9-C14 isoalkane, C9-C16 isoalkane, C10-C11 isoalkane, C10-C12 isoalkane, C10-C13 isoalkane, isoalkane, C11-C13 isoalkane, C11-C14 isoalkane, C12-C14 isoalkane, C12-C20 isoalkane, C13-C14 isoalkane, C13-C16 isoalkane, C14-C16 isoalkane, C15-C19 isoalkane, isododecane, and a mixture thereof; and (c)(ii) about 1 to about 25 wt. %, preferably about 5 to about 25 wt. %, more preferably about 5 to about 20 wt. % of one or more silicone-based oils, preferably selected from polydimethylsiloxane (dimethicone), dimethiconol, amodimethicone, phenyl-modified silicone, silicone block copolymers containing amine groups or quat groups or other charged or uncharged silicone block copolymers, more preferably a combination of dimethicone and dimethiconol;

(d) at least 0.5% to about 5 wt. %, preferably at least 0.5 to about 3 wt. %, more preferably about 0.8 to about 3 wt. % of one or more C1-C9 non-polymeric and non-thiol, mono-, di-, and/or tri-carboxylic acids, a salt thereof, or a combination thereof, preferably selected from formic acid, acetic acid, lactic acid, propionic acid, butyric acid, gluconic acid, valeric acid, caproic acid, enthantic acid, caprylic acid, pelargonic acid, capric acid, undecylic acid, lauric acid, tridecylic acid, lauric acid, tridecylic acid, myristic acid, pentadecylic acid, palmitic acid, margaric acid, stearic acid, nonadecylic acid, and arachidic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, and 2,6-naphthalene dicarboxylic acid, citric acid, isocitric acid, aconitric acid, propane-1,2,3-tricarboxylic acid, and benzene-1,3,5-tricarboxylic acid, a salt thereof, and a combination thereof, more preferably citric acid and optionally one or more additional C1-C9 non-polymeric and non-thiol, mono-, di-, and/or tri-carboxylic acids, a salt thereof, or a combination thereof;

(e) about 1 to about 10 wt. %, preferably about 1 to about 8, more preferably about 1 to about 5 wt. % of one or more emulsifiers, preferably one or more silicone-based emulsifiers and one or more non-silicone emulsifiers, more preferably (e)(i) about 0.1 to about 10 wt. %, more preferably about 0.5 to about 8 wt. %, more preferably about 1 to about 5 wt. % of one or more silicone-based emulsifiers selected from PEG-10 dimethicone, PEG-12 dimethicone, PEG-14 dimethicone, PEG-17 dimethicone, PPG-12 dimethicone, PPG-17 dimethicone, and derivatized/functionalized forms thereof such as Bis-PEG/PPG-20/20 dimethicone bis-PEG/PPG-16/16 PEG/PPG-16/16 dimethicone, PEG/PPG-14/4 dimethicone, PEG/PPG-20/20 dimethicone, PEG/PPG-20/23 dimethicone, and perfluorononylethyl carboxydecyl PEG-10 dimethicone, and a combination thereof, preferably PEG-14 dimethicone; and (e)(ii) about 0.01 to about 8 wt. %, more preferably about 0.1 to about 5 wt. %, more preferably about 0.5 to about 5 wt. % of one or more non-silicone emulsifiers selected from hydrogenated castor oil (e.g., PEG-60 hydrogenated castor oil), oxyethylenated fatty alcohols having an average degree of ethoxylation of 2 to 29, and a combination thereof;

(f) about 0.01 to about 5 wt. %, preferably about 0.1 to about 5 wt. %, more preferably about 0.5 to about 3 wt.

% of one or more thickening agents, preferably one or more polymeric thickening agents, more preferably selected from polyacrylamides;

(g) optionally, up to about 5 wt. %, preferably about 0.1 to about 5 wt. %, more preferably about 0.5 to about 5 wt. %, more preferably about 1 to about 3 wt. % of one or more humectants, preferably wherein at least one or the one or more humectants is selected from hydroxyalkyl ureas, preferably one or more hydroxyethyl ureas selected from selected from N-(2-hydroxyethyl) urea, N-(2-hydroxypropyl) urea, N-(3-hydroxypropyl) urea, N-(2,3-dihydroxypropyl) urea, N-(2,3,4,5,6-pentahydroxyhexyl) urea, N-methyl-N-(1,3,4,5,6-pentahydroxy-2-hexyl) urea, N-methyl-N'-(1-hydroxy-2-methyl-2-propyl) urea, N-(1-hydroxy-2-methyl-2-propyl) urea, N-(1,3-dihydroxy-2-propyl) urea; N-(trishydroxymethylmethyl) urea, N-ethyl-N'-(2-hydroxyethyl) urea, N,N-bis-(2-hydroxy-ethyl) urea, N,N'-bis-(2-hydroxyethyl) urea, N,N-bis-(2-hydroxypropyl) urea, N,N'-bis-(2-hydroxypropyl) urea, N,N-bis-(2-hydroxyethyl)-N'-propyl urea, N,N-bis-(2-hydroxypropyl)-N'-(2-hydroxyethyl) urea, N-tert-butyl-N'-(2-hydroxyethyl)-N'-(2-hydroxypropyl) urea, N-(1,3-dihydroxy-2-propyl)-N'-(2-hydroxyethyl) urea, N,N-bis-(2-hydroxyethyl)-N',N'-dimethyl urea, N,N,N',N'-tetrakis-(2-hydroxyethyl) urea, N',N'-bis-(2-hydroxyethyl)-N',N'-bis-(2-hydroxypropyl) urea, more preferably hydroxyethyl urea; and (h) optionally, up to about 5 wt. %, preferably about 0.1 to about 5 wt. %, more preferably about 1 to about 5 wt. % of one or more miscellaneous ingredients, preferably one or more miscellaneous ingredients selected from antioxidants, buffers, fragrances, preservatives, solid fatty compounds, composition colorants, fillers, vegetal extracts, or a combination thereof;

wherein the ratio of ((a)+(b)) to (c) is 1:1 to 1:5, preferably about 1:2 to about 1:5, more preferably about 1:2 to about 1:4;

the composition is translucent or transparent; and the composition has a pH of about 3 to about 6.

all percentages by weight are relative to a total weight of the composition.

In various embodiments, the leave-on hair treatment composition comprises or consists of:

(a) about 5 to about 30 wt. %, preferably about 5 to about 25 wt. %, more preferably about 5 to about 20 wt. % of water;

(b) about 10 to about 40 wt. %, more preferably about 10 to about 30 wt. %, more preferably about 15 to about 25 wt. % of glycerin and one or more additional polyols chosen from ethylene glycol, propylene glycol, butylene glycol, hexylene glycol, pentylene glycol, diethylene glycol, dipropylene glycol, 1,3 propanediol, and a mixture thereof, more preferably glycerin and dipropylene glycol;

(c) about 35 to about 75 wt. % of one or more oils, preferably about 40 to about 70 wt. %, more preferably about 45 to about 65 wt. % of oil, wherein the oil comprises or consists of:

(c)(i) about 30 to about 60 wt. %, preferably about 35 to about 55 wt. %, more preferably about 35 to about 50 wt. % of one or more hydrocarbon-based oils, preferably one or more hydrocarbon-based oils selected C9-C12 alkane, C10-C13 alkane, alkane, C12-C17 alkane, C13-C15 alkane, C14-C17 alkane, C14-C19 alkane, C14-C20 alkane, C14-C22 alkane, C15-C19 alkane, C21-C28 alkane, C17-C23 alkane, C9-C12 isoalkane, C9-C13 isoalkane, C9-C14 isoalkane, C9-C16 isoalkane, C10-C11 isoalkane, C10-C12 isoalkane, C10-C13 isoalkane, isoalkane, C11-C13 isoalkane, C11-C14 isoalkane, C12-C14 isoalkane, C12-C20 isoalkane, C13-C14 isoalkane, C13-C16 isoalkane, C14-C16 isoalkane, C15-C19 isoalkane, isododecane, and a mixture thereof; and (c)(ii) about 1 to about 25 wt. %, preferably about 5 to about 25 wt. %, more preferably about 5 to about 20 wt. % of polydimethylsiloxane (dimethicone), dimethiconol, and a combination thereof;

(d) at least 0.5% to about 5 wt. %, preferably at least 0.5 to about 3 wt. %, more preferably about 0.8 to about 3 wt. % of lactic acid, malonic acid, malic acid, tartaric acid, maleic acid, isophthalic acid, citric acid, isocitric acid, aconitric acid, propane-1,2,3-tricarboxylic acid, a salt thereof, and a combination thereof, more preferably citric acid and optionally one or more additional C1-C9 non-polymeric and non-thiol, mono-, di-, and/or tri-carboxylic acids, a salt thereof, or a combination thereof;

(e) about 1 to about 10 wt. %, preferably about 1 to about 8, more preferably about 1 to about 5 wt. % of emulsifiers, wherein the emulsifiers comprise or consist of:

(e)(i) about 0.1 to about 10 wt. %, more preferably about 0.5 to about 8 wt. %, more preferably about 1 to about 5 wt. % of one or more silicone-based emulsifiers selected from PEG-10 dimethicone, PEG-12 dimethicone, PEG-14 dimethicone, PEG-17 dimethicone, PPG-12 dimethicone, PPG-17 dimethicone, and derivatized/functionalized forms thereof such as Bis-PEG/PPG-20/20 dimethicone bis-PEG/PPG-16/16 PEG/PPG-16/16 dimethicone, PEG/PPG-14/4 dimethicone, PEG/PPG-20/20 dimethicone, PEG/PPG-20/23 dimethicone, and perfluorononylethyl carboxydecyl PEG-10 dimethicone, and a combination thereof, preferably PEG-14 dimethicone; and (e)(ii) about 0.01 to about 8 wt. %, more preferably about 0.1 to about 5 wt. %, more preferably about 0.5 to about 5 wt. % of one or more non-silicone emulsifiers selected from hydrogenated castor oil (e.g., PEG-60 hydrogenated castor oil), oxyethylenated fatty alcohols having an average degree of ethoxylation of 2 to 29, and a combination thereof;

(f) about 0.01 to about 5 wt. %, preferably about 0.1 to about 5 wt. %, more preferably about 0.5 to about 3 wt. % of one or more thickening agents, preferably one or more polymeric thickening agents, more preferably selected from polyacrylamides;

(g) optionally, up to about 5 wt. %, preferably about 0.1 to about 5 wt. %, more preferably about 0.5 to about 5 wt. %, more preferably about 1 to about 3 wt. % of one or more humectants, preferably wherein at least one or the one or more humectants is selected from hydroxyalkyl ureas, preferably one or more hydroxyethyl ureas selected from selected from N-(2-hydroxyethyl) urea, N-(2-hydroxypropyl) urea, N-(3-hydroxypropyl) urea, N-(2,3-dihydroxypropyl) urea, N-(2,3,4,5,6-pentahydroxyhexyl) urea, N-methyl-N-(1,3,4,5,6-pentahydroxy-2-hexyl) urea, N-methyl-N'-(1-hydroxy-2-methyl-2-propyl) urea, N-(1-hydroxy-2-methyl-2-propyl) urea, N-(1,3-dihydroxy-2-propyl) urea; N-(trishydroxymethylmethyl) urea, N-ethyl-N'-(2-hydroxyethyl) urea, N,N-bis-(2-hydroxy-ethyl) urea, N,N'-bis-(2-hydroxyethyl) urea, N,N-bis-(2-hydroxypropyl) urea, N,N'-bis-(2-hydroxypropyl) urea, N,N-bis-(2-hydroxyethyl)-N'-propyl urea, N,N-bis-(2-hydroxypropyl)-N'-(2-hydroxyethyl) urea, N-tert-butyl-N'-(2-hydroxyethyl)-N'-(2-hydroxypropyl) urea, N-(1,3-dihydroxy-2-propyl)-N'-(2-hydroxyethyl) urea, N,N-bis-(2-hydroxyethyl)-N',N'-dimethyl urea, N,N,N',N'-tetrakis-(2-hydroxyethyl) urea, N',N'-bis-(2-hydroxyethyl)-N',N'-bis-(2-hydroxypropyl) urea, more preferably hydroxyethyl urea; and (h) optionally, up to about 5 wt. %, preferably about 0.1 to about 5 wt. %, more preferably about 1 to about 5 wt. % of one or more miscellaneous ingredients, preferably one or more miscellaneous ingredients selected from antioxidants, buffers, fragrances, preservatives, solid fatty compounds, composition colorants, fillers, vegetal extracts, or a combination thereof;

wherein the ratio of ((a)+(b)) to (c) is 1:1 to 1:5, preferably about 1:2 to about 1:5, more preferably about 1:2 to about 1:4;

the composition is translucent or transparent; and the composition has a pH of about 3 to about 6.

all percentages by weight are relative to a total weight of the composition.

Oils

The term "oil" means any fatty substance that is in liquid form at room temperature (25° C.) and at atmospheric pressure.

Non-Volatile Oils

The non-volatile oils may be chosen especially from non-volatile hydrocarbon-based, fluoro and/or silicone oils.

Non-volatile hydrocarbon-based oils that may especially be mentioned include:

hydrocarbon-based oils of animal origin, hydrocarbon-based oils of plant origin, such as phytostearyl esters, such as phytostearyl oleate, phytostearyl isostearate and lauroylloctyldodecyl/phytostearyl glutamate (Ajinomoto, Eldew PS203), triglycerides formed from fatty acid esters of glycerol, in particular in which the fatty acids may have chain lengths ranging from C4 to C36 and especially from C18 to C36, these oils possibly being linear or branched, and saturated or unsaturated; these oils may especially be heptanoic or octanoic triglycerides, shea oil, alfalfa oil, poppy oil, millet oil, barley oil, rye oil, candlenut oil, passionflower oil, shea butter, aloe vera oil, sweet almond oil, peach stone oil, groundnut oil, argan oil, avocado oil, baobab oil, borage oil, broccoli oil, calendula oil, camelina oil, canola oil, carrot oil, safflower oil, flax oil, rapeseed oil, cotton oil, coconut oil, marrow seed oil, wheatgerm oil, jojoba oil, lily oil, macadamia oil, corn oil, meadowfoam oil, St John's Wort oil, monoi oil, hazelnut oil, apricot kernel oil, walnut oil, olive oil, evening primrose oil, palm oil, blackcurrant pip oil, kiwi seed oil, grapeseed oil, pistachio oil, winter squash oil, pumpkin oil, quinoa oil, musk rose oil, sesame oil, soybean oil, sunflower oil, castor oil and watermelon oil, and mixtures thereof, or alternatively caprylic/capric acid triglycerides, such as those sold by the company STEARINERIES DUBOIS or those sold under the names MIGLYOL 810®, 812® and 818® by the company Dynamit Nobel;

synthetic ethers containing from 10 to 40 carbon atoms, such as dicaprylyl ether;

synthetic esters, for instance oils of formula R1 COOR2, in which R1 represents a linear or branched fatty acid residue containing from 1 to 40 carbon atoms, and R2 represents a hydrocarbon-based chain that is especially branched, containing from 1 to 40 carbon atoms provided that R1+R2≥10. The esters may be chosen especially from alcohol fatty acid esters, for instance cetostearyl octanoate, Isopropyl alcohol esters, such as isopropyl myristate, isopropyl palmitate, ethyl palmitate, 2-ethylhexyl palmitate, isopropyl stearate, octyl stearate, hydroxylated esters, for instance isostearyl lactate, octyl hydroxystearate, alcohol or polyalcohol ricinoleates, hexyl laurate, neopentanoic acid esters, for instance isodecyl neopentanoate, isotridecyl neopentanoate, and isononanoic acid esters, for instance isononyl isononanoate and isotridecyl isononanoate;

polyol esters and pentaerythritol esters, for instance dipentaerythrityl tetrahydroxystearate/tetraisostearate;

fatty alcohols that are liquid at room temperature, with a branched and/or unsaturated carbon-based chain containing from 12 to 26 carbon atoms, for instance 2-octyldodecanol, isostearyl alcohol and oleyl alcohol;

C12-C22 higher fatty acids, such as oleic acid, linoleic acid or linolenic acid, and mixtures thereof;

dialkyl carbonates, the two alkyl chains possibly being identical or different, such as dicaprylyl carbonate sold under the name CETIOL CC® by Cognis; and oils of high molar mass, in particular with a molar mass ranging from about 400 to about 2000 g/mol and in particular from about 650 to about 1600 g/mol. As oils of high molar mass that may be used in the present invention, mention may be made especially of linear fatty acid esters with a total carbon number ranging from 35 to 70, for instance pentaerythrityl tetrapelargonate, hydroxylated esters, such as polyglyceryl-2 triisostearate, aromatic esters, such as tridecyl trimellitate, branched C24-C28 fatty alcohol or fatty acid esters, such as those described in U.S. Pat. No. 6,491,927, and pentaerythritol esters, and especially triisoarachidyl citrate, glyceryl triisostearate, glyceryl tris (2-decyl)tetradecanoate, polyglyceryl-2 tetraisostearate or pentaerythrityl tetrakis(2-decyl)tetradecanoate; phenyl silicones, such as Belsil PDM 1000 from the company Wacker (MM=9000 g/mol), non-volatile polydimethylsiloxanes (PDMS), PDMSs comprising alkyl or alkoxy groups that are pendent and/or at the end of the silicone chain, these groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, dimethicones or phenyl trimethicones with a viscosity of less than or equal to 100 cSt, and mixtures thereof; and also mixtures of these various oils.

Silicone-Based Oils

Useful silicone-based oils include, but are not limited to, polyorganosiloxanes, polyalkylsiloxanes, polyarylsiloxanes, polyalkarylsiloxanes, polyestersiloxanes, and a mixture thereof. Non-limiting examples include dimethicone, cyclomethicone (cyclopentasiloxane), amodimethicone, trimethyl silyl amodimethicone, phenyl trimethicone, trimethyl siloxy silicate, polymethylsilsesquioxane and a mixture thereof.

In some instances, the compositions include one or more silicones selected from the group consisting of polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), nonionic dimethicone copolyols, dimethicone copolyol esters, dimethicone copolyol quaternium nitrogen containing compounds, dimethicone copolyol phosphate esters, and mixtures thereof. Particularly preferred silicones include dimethicone, dimethiconol, amodimethicone, and a mixture thereof.

The compositions may include one or more silicone oils, for example one or more non-phenyl silicone oils and/or one or more phenyl silicone oils. The silicone oil may be apolar. An "apolar silicone oil" is intended to denote a silicone oil that does not comprise any ionic or ionisable group(s), and preferably does not comprise any oxyalkylenated($C_2$-$C_4$) unit(s) (preferably oxyethylene, oxypropylene), or glycerol unit(s).

Representative examples of non-volatile non-phenyl silicone oils which may be mentioned include polydimethylsiloxanes; alkyl dimethicones; vinylmethyl methicones; and silicones modified with aliphatic groups and/or with functional groups such as hydroxyl, thiol and/or amine groups. The non-volatile non-phenyl silicone oil is preferably chosen from non-volatile dimethicone oils. In particular, these oils can be chosen from the following non-volatile oils:
polydimethylsiloxanes (PDMSs),
PDMSs comprising aliphatic groups, in particular alkyl or alkoxy groups, which are pendent and/or at the end of the silicone chain, these groups each comprising from 2 to 24 carbon atoms. By way of example, mention may be made of the cetyl dimethicone sold under the commercial reference ABIL WAX 9801 from Evonik Goldschmidt,
PDMSs comprising aliphatic groups, or functional groups such as hydroxyl, thiol and/or amine groups,
polyalkylmethylsiloxanes substituted with functional groups such as hydroxyl, thiol and/or amine groups,
polysiloxanes modified with fatty acids, fatty alcohols or polyoxyalkylenes, and mixtures thereof.

Preferably, these non-volatile non-phenyl silicone oils are chosen from polydimethylsiloxanes; alkyl dimethicones and also PDMSs comprising aliphatic groups, in particular $C_2$-$C_{24}$ alkyl groups, and/or functional groups such as hydroxyl, thiol and/or amine groups.

The non-phenyl silicone oil may be chosen in particular from silicones of the following formula:

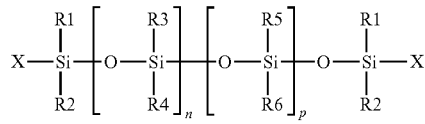

in which:
$R_1$, $R_2$, $R_5$ and $R_6$ are, together or separately, an alkyl radical containing 1 to 6 carbon atoms,
$R_3$ and $R_4$ are, together or separately, an alkyl radical containing from 1 to 6 carbon atoms, a vinyl radical, an amine radical or a hydroxyl radical,
X is an alkyl radical containing from 1 to 6 carbon atoms, a hydroxyl radical or an amine radical,
n and p are integers chosen so as to have a fluid compound, in particular of which the viscosity at 25° C. is between 9 centistokes (cSt) and 800 000 (cSt).

As non-volatile non-phenyl silicone oils which can be used according to the invention, mention may be made of those for which:
the substituents $R_1$ to $R_6$ and X represent a methyl group, and p and n are such that the viscosity is 500 000 cSt, for example the product sold under the name SE30 by the company General Electric, the product sold under the name AK 500000 by the company Wacker, the product sold under the name Mirasil DM 500 000 by the company Bluestar, and the product sold under the name Dow Corning 200 Fluid 500 000 cSt by the company Dow Corning,
the substituents $R_1$ to $R_6$ and X represent a methyl group, and p and n are such that the viscosity is 60 000 cSt, for example the product sold under the name Dow Corning 200 Fluid 60 000 CS by the company Dow Corning, and the product sold under the name Wacker Belsil DM 60 000 by the company Wacker,
the substituents $R_1$ to $R_6$ and X represent a methyl group, and p and n are such that the viscosity is 100 cSt or 350 cSt, for example the products sold respectively under the names Belsil DM100 and Dow Corning 200 Fluid 350 CS by the company Dow Corning,
the substituents $R_1$ to $R_6$ represent a methyl group, the group X represents a hydroxyl group, and n and p are such that the viscosity is 700 cSt, for example the product sold under the name Baysilone Fluid T0.7 by the company Momentive.

The total amount of silicones in the cleansing compositions can vary but is typically about 0.1 to about 10 wt. %, based on the total weight of the cleansing composition. In some instances, the total amount of silicones is about 0.1 to about 8 wt. %, about 0.1 to about 5 wt. %, about 0.5 to about 10 wt. %, about 0.5 to about 8 wt. %, or about 0.5 to about 5 wt. %, based on the total weight of the cleansing composition.

Emulsifiers

Emulsifiers are well known in the art and include amphoteric, anionic, cationic or nonionic emulsifiers, used alone or as a mixture, and optionally with a co-emulsifier.

The emulsifiers are chosen in an appropriate manner according to the emulsion to be obtained.

Non-Silicone Emulsifiers

Nonionic emulsifiers (also referred to as nonionic surfactants) are compounds well known in themselves (see, e.g., in this regard, "Handbook of Surfactants" by M. R. Porter, Blackie & Son publishers (Glasgow and London), 1991, pp. 116-178), which is incorporated herein by reference in its entirety.

The nonionic emulsifers can be, for example, selected from alcohols, alpha-diols, alkylphenols and esters of fatty acids, these compounds being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N-($C_6$-$C_{24}$)alkylglucamine derivatives, amine oxides such as ($C_{10}$-$C_{14}$)alkylamine oxides or N-($C_{10}$-$C_{14}$)acylaminopropylmorpholine oxides; and a mixture thereof.

The nonionic emulsifiers may preferably be chosen from polyoxyalkylenated or polyglycerolated nonionic emulsifiers. The oxyalkylene units are more particularly oxyethylene or oxypropylene units, or a combination thereof, and are preferably oxyethylene units.

Examples of oxyalkylenated nonionic emulsifiers that may be mentioned include: oxyalkylenated ($C_8$-$C_{24}$)alkylphenols, saturated or unsaturated, linear or branched, oxyalkylenated $C_8$-$C_{30}$ alcohols, saturated or unsaturated, linear or branched, oxyalkylenated $C_8$-$C_{30}$ amides, esters of saturated or unsaturated, linear or branched, $C_8$-$C_{30}$ acids and of polyethylene glycols, polyoxyalkylenated esters of saturated or unsaturated, linear or branched, $C_8$-$C_{30}$ acids and of sorbitol, saturated or unsaturated, oxyalkylenated plant oils, condensates of ethylene oxide and/or of propylene oxide, inter alia, alone or as mixtures.

The emulsifiers preferably contain a number of moles of ethylene oxide and/or of propylene oxide of between 2 and 100 and most preferably between 2 and 50.

In accordance with one preferred embodiment of the invention, the oxyalkylenated emulsifiers are chosen from oxyethylenated $C_8$-$C_{30}$ alcohols.

Examples of ethoxylated fatty alcohols (or $C_8$-$C_{30}$ alcohols) that may be mentioned include the adducts of ethylene oxide with lauryl alcohol, especially those containing from 9 to 50 oxyethylene groups and more particularly those containing from 10 to 25 oxyethylene groups (Laureth-10 to Laureth-25); the adducts of ethylene oxide with behenyl alcohol, especially those containing from 9 to 50 oxyethylene groups (Beheneth-9 to Beheneth-50); the adducts of ethylene oxide with cetearyl alcohol (mixture of cetyl alcohol and stearyl alcohol), especially those containing from 10 to 30 oxyethylene groups (Ceteareth-10 to Ceteareth-30); the adducts of ethylene oxide with cetyl alcohol, especially those containing from 10 to 30 oxyethylene groups (Ceteth-10 to Ceteth-30); the adducts of ethylene oxide with stearyl alcohol, especially those containing from 10 to 30 oxyethylene groups (Steareth-10 to Steareth-30); the adducts of ethylene oxide with isostearyl alcohol, especially those containing from 10 to 50 oxyethylene groups (Isosteareth-10 to Isosteareth-50); and a mixture thereof.

As examples of polyglycerolated nonionic emulsifiers, polyglycerolated $C_8$-$C_{40}$ alcohols are preferably used.

In particular, the polyglycerolated $C_8$-$C_{40}$ alcohols correspond to the following formula:

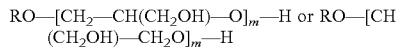
RO—[CH$_2$—CH(CH$_2$OH)—O]$_m$—H or RO—[CH(CH$_2$OH)—CH$_2$O]$_m$—H in which R represents a linear or branched $C_8$-$C_{40}$ and preferably $C_8$-$C_{30}$ alkyl or alkenyl radical, and m represents a number ranging from 1 to 30 and preferably from 1.5 to 10.

As examples of compounds that are suitable in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

According to one of the embodiments according to the present invention, the nonionic emulsifiers may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and a mixture thereof.

Examples of ethoxylated fatty esters that may be mentioned include the adducts of ethylene oxide with esters of lauric acid, palmitic acid, stearic acid or behenic acid, and a mixture thereof, especially those containing from 9 to 100 oxyethylene groups, such as PEG-9 to PEG-50 laurate; PEG-9 to PEG-50 palmitate; PEG-9 to PEG-50 stearate; PEG-9 to PEG-50 palmitostearate; PEG-9 to PEG-50 behenate; polyethylene glycol 100 EO monostearate; and a mixture thereof.

As glyceryl esters of fatty acids, glyceryl stearate (glyceryl mono-, di- and/or tristearate) (glyceryl stearate) or glyceryl ricinoleate and a mixture thereof can in particular be cited.

As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited.

Mixtures of these emulsifiers, such as for example the product containing glyceryl stearate and PEG-100 stearate, marketed under the name ARLACEL 165 by Croda, and a product containing glyceryl stearate (glyceryl mono- and distearate) and potassium stearate, can also be used.

The sorbitol esters of $C_8$-$C_{24}$ fatty acids and alkoxylated derivatives thereof can be selected from sorbitan palmitate, sorbitan trioleate and esters of fatty acids and alkoxylated sorbitan containing for example from 20 to 100 EO, such as for example polyethylene sorbitan trioleate (polysorbate 85) or the compounds marketed under the trade names Tween 20 or Tween 60 by Croda.

As esters of fatty acids and glucose or alkylglucose, in particular glucose palmitate, alkylglucose sesquistearates such as methylglucose sesquistearate, alkylglucose palmitates such as methylglucose or ethylglucose palmitate, methylglucoside fatty esters and more specifically the diester of methylglucoside and oleic acid (Methyl glucose dioleate), the mixed ester of methylglucoside and the mixture oleic acid/hydroxystearic acid (Methyl glucose dioleate/hydroxystearate), the ester of methylglucoside and isostearic acid (Methyl glucose isostearate), the ester of methylglucoside and lauric acid (Methyl glucose laurate), the mixture of monoester and diester of methylglucoside and isostearic acid (Methyl glucose sesqui-isostearate), the mixture of monoester and diester of methylglucoside and stearic acid (Methyl glucose sesquistearate) and in particular the product marketed under the name Glucate SS by Lubrizol, and a mixture thereof can be cited.

As ethoxylated ethers of fatty acids and glucose or alkylglucose, ethoxylated ethers of fatty acids and methylglucose, and in particular the polyethylene glycol ether of the diester of methylglucose and stearic acid with about 20 moles of ethylene oxide (PEG-20 methyl glucose distearate) such as the product marketed under the name GLUCAM E-20 DISTEARATE by Lubrizol, the polyethylene glycol ether of the mixture of monoester and diester of methylglucose and stearic acid with about 20 moles of ethylene oxide (PEG-20 methyl glucose sesquistearate) and in particular the product marketed under the name GLUCAMATE SSE-20 by Lubrizol, and a mixture thereof, can for example be cited.

As sucrose esters, saccharose palmito-stearate, saccharose stearate and saccharose monolaurate can for example be cited.

As sugar ethers, alkylpolyglucosides can be used, and for example decylglucoside such as the product marketed under the name MYDOL 10 by Kao Chemicals, the product marketed under the name PLATAREN 2000 by BASF, and the product marketed under the name ORAMIX NS 10 by Seppic, caprylyl/capryl glucoside such as the product marketed under the name ORAMIX CG 110 by Seppic or under the name LUTENSOL GD 70 by BASF, laurylglucoside such as the products marketed under the names PLANTAREN 1200 N and PLANTACARE 1200 by BASF, cocoglucoside such as the product marketed under the name PLANTACARE 818/UP by BASF, cetostearyl glucoside possibly mixed with cetostearyl alcohol, marketed for example under the name MONTANOV 68 by Seppic, under the name TEGO-CARE CG90 by Evonik, arachidyl glucoside, for example in the form of the mixture of arachidyl and behenyl alcohols and arachidyl glucoside marketed under the name MONTANOV 202 by Seppic, cocoylethylglucoside, for example in the form of the mixture (35/65) with cetyl and stearyl alcohols, marketed under the name MONTANOV 82 by Seppic, and a mixture thereof can in particular be cited.

Mixtures of glycerides of alkoxylated plant oils such as mixtures of ethoxylated (200 EO) palm and copra (7 EO) glycerides can also be cited.

The nonionic emulsifiers may be selected from the group consisting of PEG-7 glyceryl cocoate, PEG-20 methylglucoside sesquistearate, PEG-20 glyceryl tri-isostearate, PG-5 dioleate, PG-4 diisostearate, PG-10 isostearate, PEG-8 isostearate, and PEG-60 hydrogenated castor oil.

Mixtures of these oxyethylenated derivatives of fatty alcohols and of fatty esters may also be used.

In some case, the nonionic emulsifiers is a fatty alkanolamide. Non-limiting examples of fatty alkanolamides that may be used include cocamide MEA, cocamide DEA, soyamide DEA, lauramide DEA, oleamide MIPA, stearamide MEA, myristamide DEA, stearamide DEA, oleylamide DEA, tallowamide DEA lauramide MIPA, tallowamide MEA, isostearamide DEA, isostearamide MEA, and a mixture thereof.

Silicone-Based Emulsifiers

In some instance, the one or more emulsifiers include an oganosiloxane emulsifier, including crosslinked organosiloxane emulsifiers. For example, the compositions may comprise one or more crosslinked organosiloxane emulsifier selected from the group consisting of dimethicone/dimethicone PEG/PPG 15 crosspolymer, dimethicone PEG-10 crosspolymer, dimethicone PEG-10/15 crosspolymer, dimethicone PEG-15 crosspolymer, dimethicone polyglycerin-3 crosspolymer, dimethicone PPG-20 crosspolymer, dimethiconol/methylsilanol/silicate crosspolymer; dimethiconol/silicate crosspolymer, lauryl dimethicone PEG-15 crosspolymer, lauryl dimethicone polyglycerin-3 crosspolymer, PEG-8 dimethicone polysorbate-20 crosspolymer, PEG-10 dimethicone/vinyl dimethicone crosspolymer, PEG-10 lauryl dimethicone crosspolymer, PEG-15/lauryl dimethicone crosspolymer, PEG-15 laurylpolydimethylsiloxyethyl crosspolymer.

In another embodiment, the compositions include one or more linear organosiloxane emulsifier selected from the group consisting of cyclotetrasiloxane (and) cyclopentasiloxane (and) PEG/PPG-18 dimethicone, cyclopentasiloxane (and) PEG/PPG-18/18 dimethicone; PEG/PPG-18/18 dimethicone; lauryl PEG/PPG-18/18 methicone; cetyl PEG/PPG-14/14 dimethicone; bis-cetyl PEG/PPG-14/14 dimethicone; cetyl PEG/PPG-10/1 dimethicone; PEG-11 methyl ether dimethicone; PEG/PPG-20/22 butyl ether dimethicone; PEG-9 dimethicone; PEG-3 dimethicone; PEG-9 methyl ether dimethicone; PEG-10 dimethicone; lauryl PEG-9 polydimethylsiloxyethyl dimethicone.

Usable oxyalkylenated organosiloxane emulsifier include the following:

An oxyalkylenated organosiloxane emulsifier having the general formula:

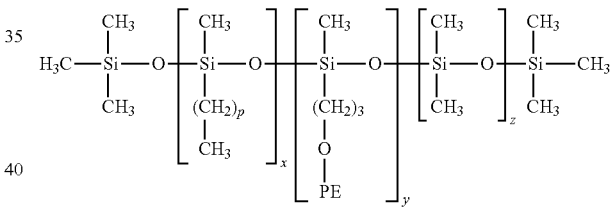

wherein p is 0-40 (the range including all numbers between and subranges such as 2, 3, 4, 13, 14, 15, 16, 17, 18, etc.), and PE is $(-C_2H_4O)_a-(-C_3H_6O)_b-H$ wherein a is 0-25, b is 0-25 with the proviso that both a and b cannot be 0 simultaneously, x, y, and z are each independently ranging from 0 to 1 million with the proviso that x and y cannot be 0 simultaneously. In some cases, x, y, z, a, and b are such that the molecular weight of the polymer ranges from about 5,000 to about 500,000, from about 10,000 to 100,000, or is about 50,000, and the polymer is generically referred to as dimethicone copolyol. In some instances, p is such that the long chain alkyl is cetyl or lauryl, and the the compound is called, generically, cetyl dimethicone copolyol or lauryl dimethicone copolyol respectively. In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or ether, such as methyl ether, ethyl ether, propyl ether, butyl ether, and the like.

An oxyalkylenated organosiloxane emulsifier having the general formula:

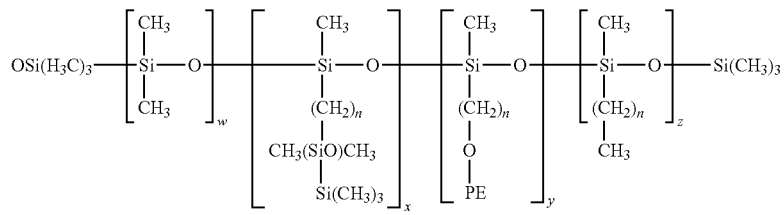

wherein each n is independently 0-100 with the proviso that there must be at least one PE radical. In some instances, where each n independently ranges from about 2 to 30, and PE $(-C_2H_4O)_a-(-C_3H_6O)_b-H$ wherein a is 0-25, b is 0-25 with the proviso that both a and b cannot simultaneously be 0; and wherein w, x, y, and z are each independently 0 to 1,000,000 with the proviso that there is at least one PE. In some embodiments the organosiloxane emulsifier is lauryl PEG-9 Polydimethylsiloxyethyl Dimethicone. Oxyalkylenated organosiloxane emulsifiers disclosed in U.S. Pat. No. 9,095,543 are useful in the instant compositions. U.S. Pat. No. 9,095,543 is incorporated herein by reference in its entirety.

Further examples of organosiloxane emulsifiers include those having C.T.F.A. names Bis-Butyldimethicone Polyglyceryl-3; Bis-PEG/PPG-14/14 Dimethicone; Bis-butyldimethicone Polyglyceryl-3; Bis-isobutyl PEG/PPG-10/7 Dimethicone copolymer; Bis-PEG/PPG-18/6 Dimethicone; Bis-PEG/PPG-20/20 Dimethicone; Bis-PEG/PPG-16/16 PEG/PPG-16/16 Dimethicone; Bis(PPG-7 Undeceneth-21-Dimethicone; Cetyl Dimethicone PEG-7 Acetate; Cetyl PEG-8 Dimethicone; Cetyl PEG/PPG-15/16 Butyl Ether Dimethicone; Cetyl PEG/PPG-15/15 Butyl Ether Dimethicone; Cetyl PEG/PPG-7/3 Dimethicone; Cetyl PEG/PPG-10/1 Dimethicone; Dimethicone PEG-15 Acetate; Dimethicone PEG-7 Cocoate; Dimethicone PEG-7 Phosphate; Dimethicone PEG-10 Phosphate; Dimethicone PEG/PPG-7/4 Phosphate; Dimethicone PEG/PPG-12/4 Phosphate; Dimethicone PEG-7 Undecylenate; Lauryl Dimethicone PEG-10 Phosphate; Isopolyglyceryl-3 Dimethicone; Isopolyglyceryl-3 Dimethiconol; Isostearyl Carboxyldecyl PEG-8 Dimethicone; Lauryl Methicone PEG-10 Phosphate; Lauryl PEG-8 Dimethicone; Lauryl PEG-10 Methyl Ether Dimethicone; Lauryl PEG/PPG-18/18 Methicone; PEG-6 Methyl Ether Dimethicone; PEG-7 Methyl Ether Dimethicone; PEG-9 Methyl Ether Dimethicone; PEG-10 Methyl Ether Dimethicone; PEG-11 Methyl Ether Dimethicone; PEG-11 Methyl Ether Dimethicone; PEG-32 Methyl Ether Dimethicone; PEG-PEG/PPG-28/21 Acetate Dimethicone; PEG/PPG-22/22 Butyl Ether Dimethicone; PEG/PPG-23/23 Butyl Ether Dimethicone; PEG/PPG-24/18 Butyl Ether Dimethicone; PEG/PPG-3/10 Dimethicone; PEG/PPG-4/12 Dimethicone; PEG/PPG-6/11 Dimethicone; PEG/PPG-8/14 Dimethicone; PEG/PPG-12/16 Dimethicone; PEG/PPG-12/18 Dimethicone; PEG/PPG-14/4 Dimethicone; PEG/PPG-15/5 Dimethicone; PEG/PPG-15/15 Dimethicone; PEG/PPG-16/2 Dimethicone; PEG/PPG-16/8 Dimethicone; PEG/PPG-17/18 Dimethicone; PEG/PPG-18/12 Dimethicone; PEG/PPG-19/19 Dimethicone; PEG/PPG-20/6 Dimethicone; PEG/PPG-20/15 Dimethicone; PEG/PPG-20/20 Dimethicone; PEG/PPG-20/29 Dimethicone; PEG/PPG-22/23 Dimethicone; PEG/PPG-22/24 Dimethicone; PEG/PPG-25/25 Dimethicone; PEG/PPG-27/27 Dimethicone; PEG/PPG-30/10 Dimethicone; PEG/PPG-10/3 Oleyl Ether Dimethicone; PEG-8 trisiloxane; Polyglyceryl-3 Polydimethylsiloxyethyl Dimethicone; PPG-12 Butyl Ether Dimethicone; Silicone Quaternium-17; TEA-Dimethicone PEG-7 Phosphate; or mixtures thereof.

Further examples of commercial linear organosiloxane emulsifiers are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

Also suitable are various types of fully or partially cross-linked oxyalkylenated organosiloxane emulsifiers. They may be elastomeric or non-elastomeric. They are sometimes referred to as "emulsifying elastomers" because of they have both elastomeric and emulsifying properties.

Polyoxyalkylenated silicone elastomers that may be used in at least one embodiment include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers include dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

Further examples of crosslinked organosiloxane emulsifiers include, but are not limited to Dimethicone/dimethicone PEG/PPG 15 crosspolymer; Dimethicone PEG-10 crosspolymer; Dimethicone PEG-10/15 Crosspolymer; Dimethicone PEG-15 Crosspolymer; Dimethicone Polyglycerin-3 Crosspolymer; Dimethicone PPG-20 Crosspolymer; Dimethiconol/Methylsilanol/Silicate Crosspolymer; Dimethiconol/Silicate Crosspolymer; Lauryl Dimethicone PEG-15 Crosspolymer; Lauryl Dimethicone Polyglycerin-3 Crosspolymer; PEG-8 Dimethicone Polysorbate-20 Crosspolymer; PEG-10 Dimethicone/Vinyl Dimethicone Crosspolymer; PEG-10 Lauryl Dimethicone Crosspolymer; PEG-15/Lauryl Dimethicone Crosspolymer; and PEG-15 Laurylpolydimethylsiloxyethyl Crosspolymer.

Thickening Agents

Thickening agents that may be mentioned include the following:
a. Carboxylic acid or carboxylate based homopolymer or co-polymer, which can be linear or crosslinked: These polymers contain one or more monomers derived from acrylic acid, substituted acrylic acids, and salts and esters of these acrylic acids (acrylates) and the substituted acrylic acids. Commercially available polymers include those sold under the trade names CARBOPOL, ACRYSOL, POLYGEL, SOKALAN, CARBOPOL ULTREZ, and POLYGEL. Examples of commercially available carboxylic acid polymers include the carbomers, which are homopolymers of acrylic acid crosslinked with allyl ethers of sucrose or pentaerytritol. The carbomers are available as the CARBOPOL 900 series from B.F. Goodrich (e.g., CARBOPOL 954). In addition, other suitable carboxylic acid polymeric agents include ULTREZ 10 (B.F. Goodrich) and copolymers of $C_{10}$-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as CARBOPOL 1342, CARBOPOL 1382, PEMULEN TR-1, and PEMULEN TR-2, from B.F. Goodrich.

Other suitable carboxylic acid or carboxylate polymeric agents include copolymers of acrylic acid and alkyl $C_5$-$C_{10}$ acrylate, copolymers of acrylic acid and maleic anhydride, and polyacrylate crosspolymer-6. Polyacrylate Crosspolymer-6 is aviable in the raw material known as SEPIMAX ZEN from Seppic.

Another suitable carboxylic acid or carboxylate polymeric agent includes acrylamidopropyltrimonium chloride/acrylates copolymer, a cationic acrylates copolymer (or a quaternary ammonium compound), available as a raw maerial known under the tradename of SIMULQUAT HC 305 from Seppic.

In certain embodiments, the carboxylic acid or carboxylate polymer thickeners useful herein are those selected from carbomers, acrylates/C10-C30 alkyl acrylate crosspolymers, polyacrylate crosspolymer-6, acrylamidopropyltrimonium chloride/acrylates copolymer, and mixtures thereof.
b. Celluloses: Non-limiting examples of celluloses include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. In some instances, the cellulose is selected from water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt). Furthermore, in some instance, the cellulose is preferably hydroxypropylcellulose (HPC).
c. Polyvinylpyrrolidone (PVP) and co-polymers: Non-limiting examples include Polyvinylpyrrolidone(PVP), Polyvinylpyrrolidone(PVP)/vinyl acetate copolymer (PVP/VA copolymer), polyvinylpyrrolidone (PVP)/eicosene copolymer, PVP/hexadecene copolymer, etc. Commercially available polyvinylpyrrolidone includes LUVISKOL K30, K85, K90 available from BASF. Commerically available copolymers of vinylpyrrolidone and vinylacetate include LUVISKOL VA37, VA64 available from BASF; copolymers of vinylpyrrolidone, methacrylamide, and vinylimidazole (INCI: VP/Methacrylamide/Vinyl Imidazole Copolymer) is commercially available as LUVISET from BASF. In some instances, PVP and PVP/VA copolymer are preferred.
d. Sucrose esters: Non-limiting examples include sucrose palmitate, sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose pentaoleate, sucrose hexaoleate, sucrose heptaoleate or sucrose octooleate, and mixed esters, such as sucrose palmitate/stearate, and mixtures thereof.
e. Polyglyceryl esters: Non-limiting polyglycerol esters of fatty acids (polygylceryl esters) include those of the following formula:

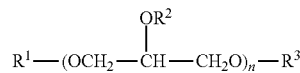

wherein n is from 2 to 20 or from 2 to 10 or from 2 to 5, or is 2, 3, 4, 5, 6, 7, 8, 9, or 10, and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and mixtures thereof.
f. C8-24 hydroxyl substituted aliphatic acid and C8-24 conjugated aliphatic acid: Non-limiting examples include conjugated linoleic acid, cis-parinaric acid, trans-7-octadecenoic acid, cis-5,8,11,14,17-eicosapentanoic acid, cis-4,7,10,13,16,19-docosahexenoic acid, columbinic acid, linolenelaidic acid, ricinolaidic acid, stearidonic acid, 2-hydroxystearic acid, alpha-linolenic acid, arachidonic acid, cis-11,14-eicosadienoic acid, linolelaidic acid, monopetroselinic acid, petroselinic acid, ricinoleic acid, trans-vaccenic acid, cis-11,14,17-eicosatrienoic acid, cis-5-eicosenoic acid, cis-8,11,14-eicosatrienoic acid, hexadecatrienoic acid, palmitoleic acid, petroselaidic acid, trans trans farnesol, cis-13,16-docosadienoic acid, cis-vaccenic acid, cis-11-eicosenoic acid, cis-13,16,19-docosatrienoic acid, cis-13-octadecenoic acid, cis-15-octadecanoic acid, cis-7,10,13,16 docosatetraenoic acid, elaidic acid, gamma-linolenic acid, geranic acid, geranyl geranoic acid, linoleic acid, oleic acid, pinolenic acid, trans-13-octadecenoic acid. More preferably, the aliphatic acid comprises 12-hydroxystearic acid, conjugated linoleic acid, or a mixture thereof.

g. Gums: Non-limiting examples of gums include gum arabic, tragacanth gum, karaya gum, guar gum, gellan gum, tara gum, locust bean gum, tamarind gum, xanthan gum, locust bean gum, Seneca gum, *sclerotium* gum, gellan gum, etc.

The leave-on hair treatment compositions of the instant disclosure optionally include or exclude cationic surfactants, anionic surfactants, and/or amphoteric surfactants. In various embodiments, the leave-on hair treatment composition is free or essentially free from cationic surfactants. In various embodiments, the leave-on hair treatment composition is free or essentially free from anionic surfactants. In various embodiments, the leave-on hair treatment composition is free or essentially free from amphoteric surfactants.

In various embodiments, the leave-on hair treatment composition is free or essentially free from reducing agents, oxidizing agents, oxidative dye precursors, direct dyes, or a combination thereof. In various embodiments, the leave-on hair treatment composition is free or essentially free from reducing agents. In various embodiments, the leave-on hair treatment composition is free or essentially free from oxidizing agents (such as hydrogen peroxide), in various embodiments, the leave-on hair treatment composition is free or essentially free from direct dyes.

Various changes can be made in the above-described compositions and methods without departing from the scope of the invention. Accordingly, it is intended that all disclosure contained in the above description and in the examples given below, shall be interpreted as illustrative and not in a limiting sense.

| | | | Example 1 (Inventive Compositions) | |
|---|---|---|---|---|
| | | | A wt. % 1239858 I | B wt. % 1045612 D2 |
| (a) | Water | WATER | 12.7 | 12.4 |
| (b) | Polyol | PROPYLENE GLYCOL | 0.1 | 0.1 |
| | | GLYCERIN | 5 | 5 |
| | | DIPROPYLENE GLYCOL | 14 | 14 |
| | | (a) + (b) | 31.8 | 31.5 |
| (c)(i) | Hydrocarbon Oil | ISODODECANE | 42.9 | 45.2 |
| | | C13-14 ISOALKANE | 0.3 | 0.1 |
| (c)(ii) | Silicone Oil | DIMETHICONOL | 4.2 | 4.2 |
| | | DIMETHICONE | 8 | 8 |
| | | Total (c) | 51.4 | 57.5 |
| | | Ratio of ((a) + (b)):(c) | 1:1.6 | 1:1.8 |
| (d) | Carboxylic Acid | CITRIC ACID | 1 | 1 |
| (e)(i) | Silicone Emulsifier | PEG-14 DIMETHICONE | 1.9 | 1.9 |
| (e)(ii) | Non-Silicone Emulsifier | LAURETH-7 | 0.1 | 0.1 |
| | | PEG-60 HYDROGENATED CASTOR OIL | 0.5 | 0.5 |
| (f) | Monoalcohol | ETHANOL | 5.5 | 5.5 |
| (g) | Thickening Agent | POLYACRYLAMIDE | 0.6 | 0.2 |
| (h) | Humectant | HYDROXYETHYL UREA | 1.4 | 1.4 |
| (i) | Miscellaneous Ingredients | Antioxidants, Buffers, Fragrances, Preservatives, etc.* | ≤5 | ≤5 |
| | | pH | 5 | 3 |
| | | Viscosity | ~2620** | ~2080** |

*pentaerythrityl tetra-di-T-butyl hydroxyhydrocinnamate, sodium citrate, phenoxyethanol, and fragrance.
**The viscosity was measured with a Brookfield DV-LL+ Pro Viscometer using Helipath T-Bar Spindle C and rotational speed of 50% RPM.

Example 2

Performance

Testing was carried out to determine treatment with Composition A influences hair fiber. Testing was carried out on Caucasian hair swatches, treated according to one of three different treatment protocols, described below.

1. CONTROL: Hair swatches were initially cleansed with a standard shampoo (0.4 ml/g hair, 30 seconds massage, and 1 min. leave-in, rinse, and excess water squeezed out from the hair). After cleansing, the hair swatches were subjected to six treatments with deionized water. Deionized water was applied to the hair swatches six consecutive times. The hair swatches were allowed to dry after each application of deionized water.

2. INVENTIVE: Hair swatches were initially cleansed with a standard shampoo (0.4 ml/g hair, 30 seconds massage, and 1 min. leave-in, rinse, and excess water squeezed out from the hair). After cleansing, the hair swatches were subjected to six treatments with Composition A. For each treatment, Composition A was applied to the hair swatches (0.15 g/g of hair) massaged into the hair for 1 minute, combed through the hair 5 times, and the hair was blow dried using high/hot setting for about 3 minutes. The treatment process was carried out six consecutive times.

3. INVENTIVE: One week after the hair swatches were treated according to (2) above, the hair swatches were cleansed with a standard shampoo (0.4 ml/g hair, 30 seconds massage, and 1 min. leave-in, rinse, and excess water squeezed out from the hair). After cleansing the hair, the hair was blow dried using high/hot setting for about 3 minutes.

Testing was carried out to determine how the three treatment protocols described above influence the hair. The hair was analyzed with differential scanning calorimetry (DSC, DSC-2500, TA Instruments), miniature tensile testing (MTT, MTT-686, Dia-Stron Ltd), and cyclic fatigue tensile testing (CFTT, CYC802, Dia-Stron Ltd). Each individual test was carried out using fifty (50) hair fibers per treatment.

DSC was used to measure denaturation temperature, which is a measure of the thermal stability of proteins in hair.

CFTT was used to measure cycles to break (CTB), which asseses the number of repeated extensions and relaxations of the hair fiber until breakage; each extension causes a pre-specified stress that maintains the fiber deformation within the elastic region of the hair type, simulating everyday hair grooming. Improvements in this metric indicate a higher ability for the hair to resist fatigue.

MTT was used to measure Young's Modulus, i.e., slope of the initial portion of the stress-strain curve, which is adjusted for cross-sectional area, representing a measure of the hair spring-like structure. It also measures plateau stress, which is the average stress during plateau region of fiber's stress-strain curve (~15% strain); break stress, which is the total force needed to break hair fiber; break extension, which represents the total strain of hair fibers at break point; and toughness, i.e., the extent of the hair's ability to absorb energy before fracture.

Test results were subjected to statistical analysis using Turkey's fences with k=3, to determine and exclude significant outliers. Student's t-test at 95% confidence interval was used to analyze significant differences in DSC and MTT outputs. Log-Rank test at 95% confidence interval was used to analyze significant differences in cycles to break. The results are presented in the tables below and the corresponding figures. Levels not connected by the same number are statistically significant.

TABLE 1

DSC
Denaturation Temperature (° C.), 95% CI
Show in FIG. 1

| Treatment | N | Mean | Std Error | Statistical Differences |
|---|---|---|---|---|
| Control | 4 | 149.1 | 0.34 | 3 |
| 6 Treatments | 4 | 151.5 | 0.12 | 2 |
| 6 Treatments + Cleanse | 4 | 154.1 | 0.16 | 1 |

TABLE 2

Figure 2:
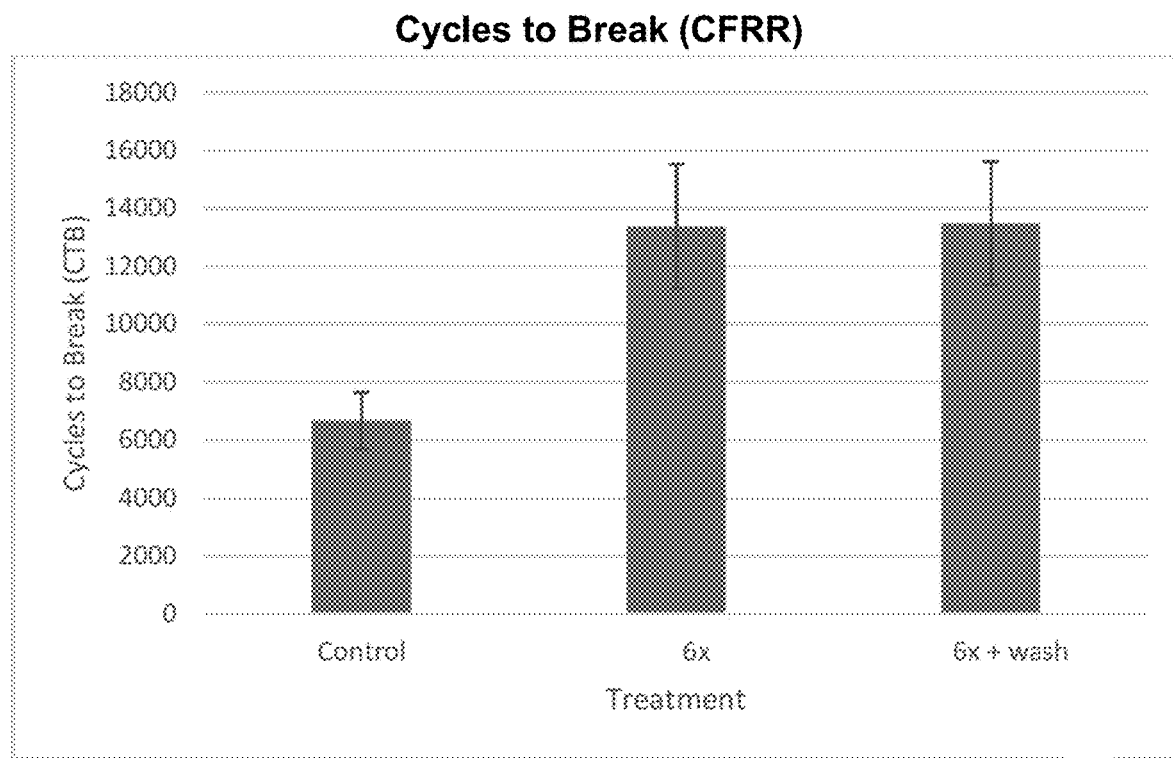
FIG. 2 is a graph showing the cycles to break (CTB) of a control, hair treated with a composition according to the instant disclosure, and hair treated with a composition of the instant disclosure and a shampoo.

CFTT
Cycles to Break (CTB)
Show in FIG. 2

| Treatment | N | Median | Mean | Std Error | Statistical Differences |
|---|---|---|---|---|---|
| Control | 50 | 4160 | 6681 | 966 | 2 |
| 6 Treatments | 48 | 8604 | 13490 | 2124 | 1 |
| 6 Treatments + Cleanse | 49 | 8762 | 13378 | 2149 | 1 |

TABLE 3

Figure 3:
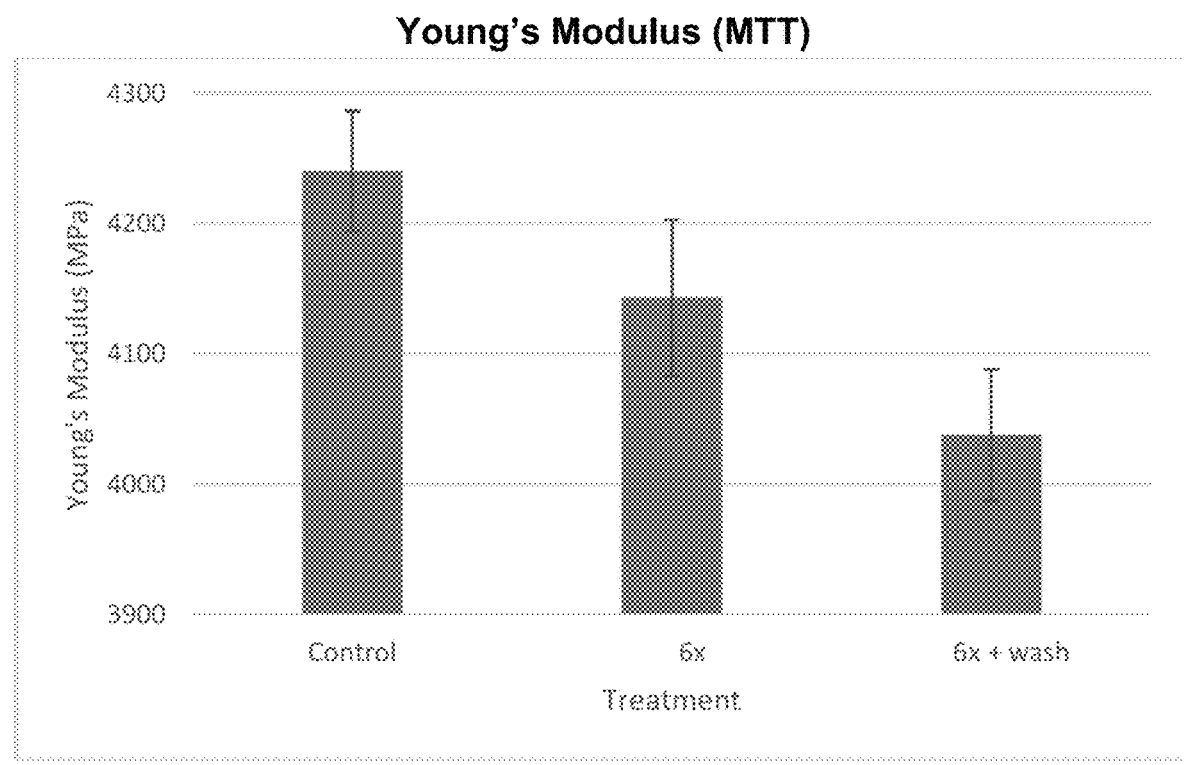
FIG. 3 is a graph showing the Young's Modulus (MTT) of a control, hair treated with a composition according to the instant disclosure, and hair treated with a composition of the instant disclosure and a shampoo.

MTT
Young's Modulus (MPa), 95% CI
Show in FIG. 3

| Treatment | N | Mean | Std Error | Statistical Differences |
|---|---|---|---|---|
| Control | 47 | 4240.4 | 46.1 | 1 |
| 6 Treatments | 48 | 4143.3 | 59.8 | 1, 2 |
| 6 Treatments + Cleanse | 48 | 4037.9 | 50.2 | 2 |

TABLE 4

Figure 4:
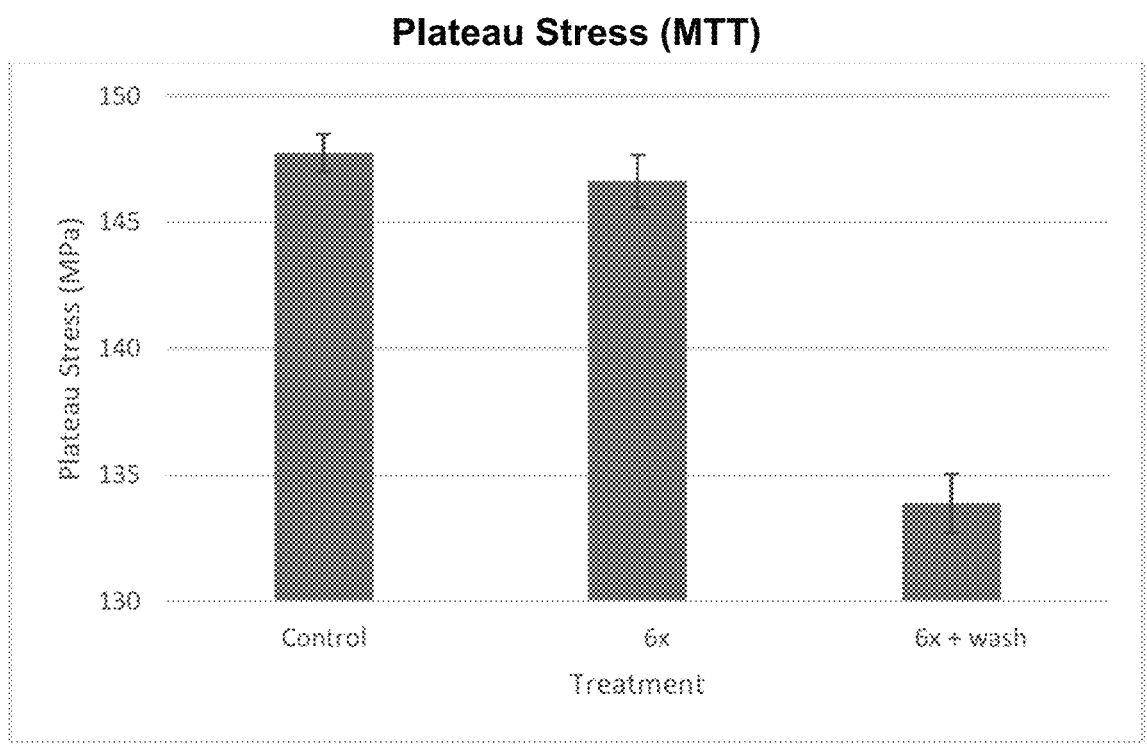
FIG. 4 is a graph showing the Plateau Stress (MTT) of a control, hair treated with a composition according to the instant disclosure, and hair treated with a composition of the instant disclosure and a shampoo.

MTT
Plateau Stress (Mpa), 95% CI
Show in FIG. 4

| Treatment | N | Mean | Std Error | Statistical Differences |
|---|---|---|---|---|
| Control | 47 | 147.7 | 0.74 | 1 |
| 6 Treatments | 48 | 146.6 | 1.04 | 1 |
| 6 Treatments + Cleanse | 48 | 133.9 | 1.16 | 2 |

TABLE 5

Figure 5:
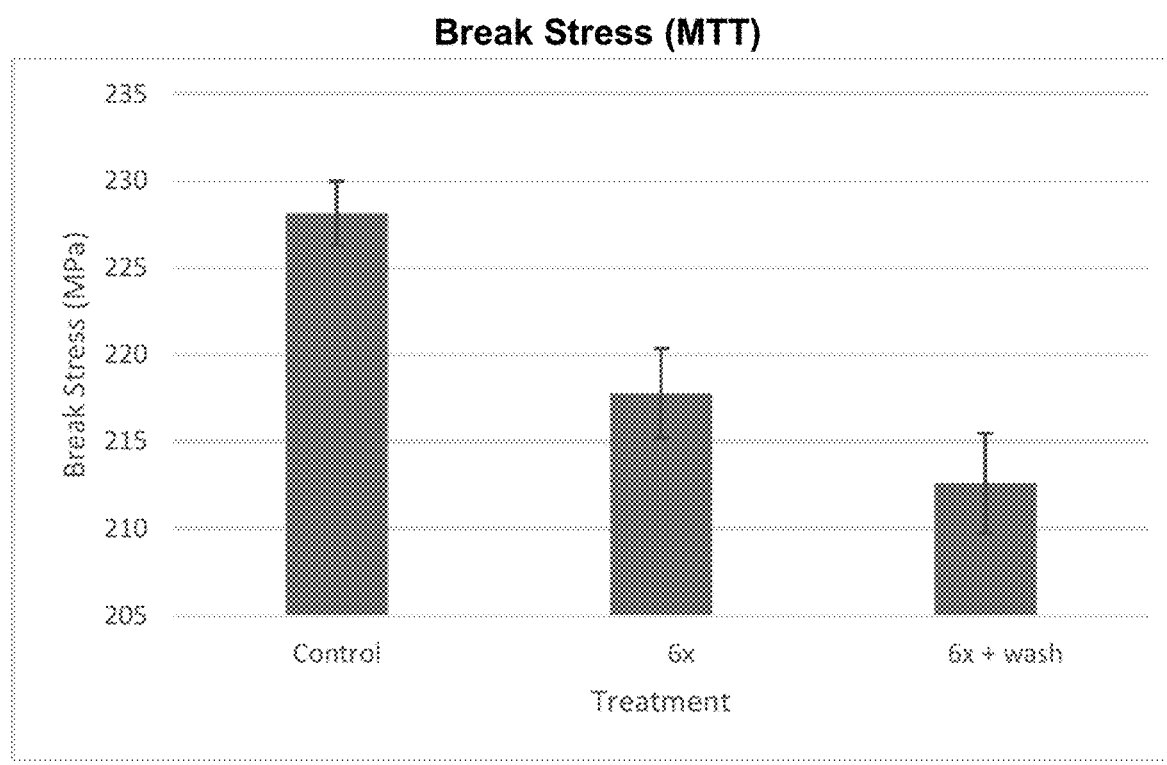
FIG. 5 is a graph showing the Break Stress (MTT) of a control, hair treated with a composition according to the instant disclosure, and hair treated with a composition of the instant disclosure and a shampoo.

MTT
Break Stress (MPa), 95% CI
Show in FIG. 5

| Treatment | N | Mean | Std Error | Statistical Differences |
|---|---|---|---|---|
| Control | 47 | 228.1 | 1.84 | 1 |
| 6 Treatments | 48 | 217.8 | 2.57 | 2 |
| 6 Treatments + Cleanse | 48 | 212.6 | 2.88 | 2 |

TABLE 6

Figure 6:
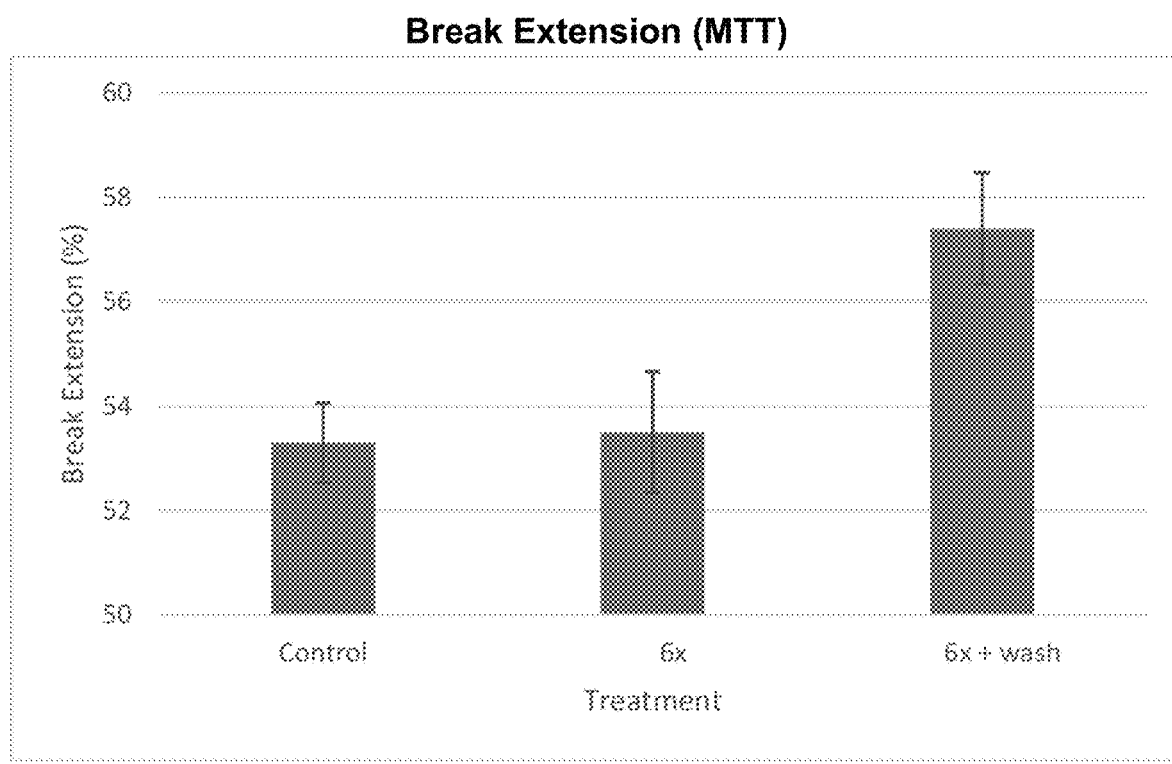
FIG. 6 is a graph showing the Break Extension (MTT) of a control, hair treated with a composition according to the instant disclosure, and hair treated with a composition of the instant disclosure and a shampoo.

MTT
Break Extension (%), 95% CI
Show in FIG. 6

| Treatment | N | Mean | Std Error | Statistical Differences |
|---|---|---|---|---|
| Control | 48 | 53.3 | 1.07 | 2 |
| 6 Treatments | 48 | 53.5 | 1.16 | 2 |
| 6 Treatments + Cleanse | 47 | 57.4 | 0.75 | 1 |

TABLE 7

Figure 7:
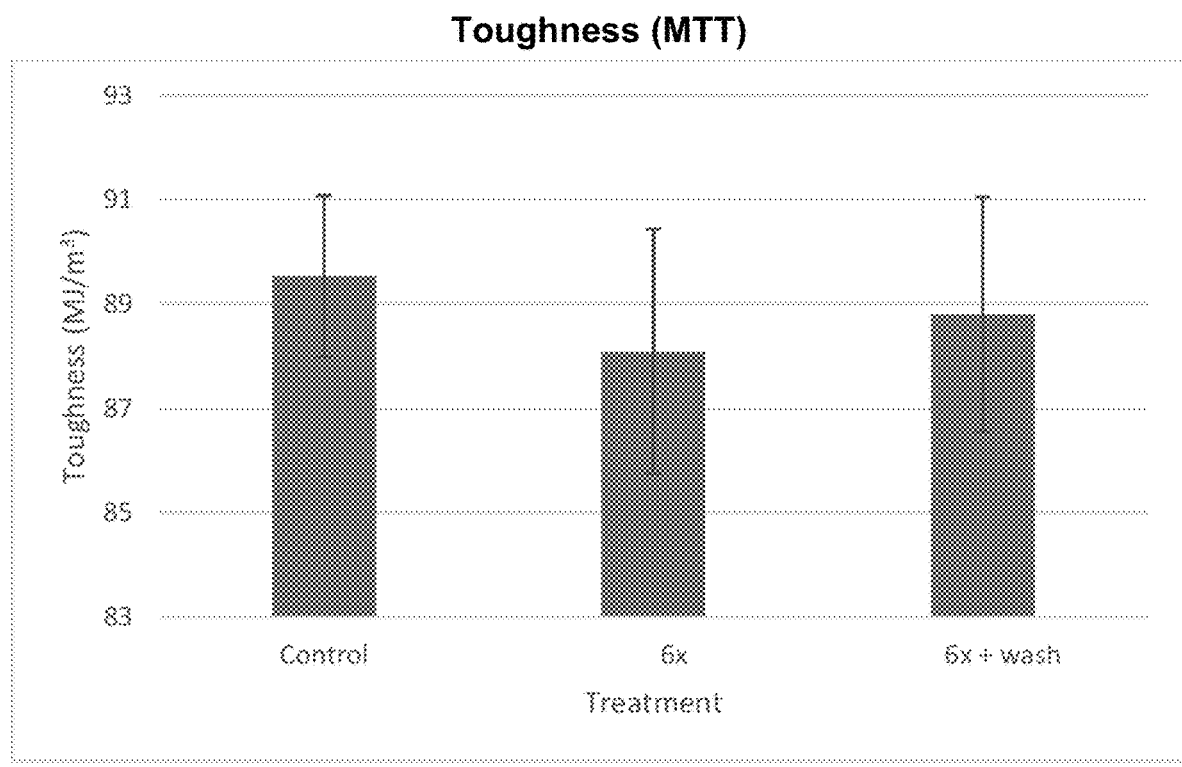
FIG. 7 is a graph showing the Toughness (MTT) of a control, hair treated with a composition according to the instant disclosure, and hair treated with a composition of the instant disclosure and a shampoo.

MTT
Toughness (Mj/m3), 95% CI
Show in FIG. 7

| Treatment | N | Mean | Std Error | Statistical Differences |
|---|---|---|---|---|
| Control | 47 | 89.5 | 1.55 | 1 |
| 6 Treatments | 48 | 88.8 | 2.25 | 1 |
| 6 Treatments + Cleanse | 48 | 88.1 | 2.35 | 1 |

The data show that hair treated according to Protocol (2) (6 treatments) modifies the hair fiber and improves durability versus hair treated according to Protocol (1) (Control). Hair treated according to Protocol (2) (6 treatments) also appears to improve hydration and moisturization of the hair fiber, leading to a lower break stress versus Protocol (1) (Control), due to solvation of weak bonds. Hair treated according to Protocol (3) (6 treatments and cleanse) sustained the benefits provided by Protocol (2) (6 treatments). This indicates that Composition A penetrates deep into the hair fiber with improved retention. Hair treated with Protocol (3) (6 treatment and cleanse) exhibited a lower plateau stress and higher break extension than hair treated with Protocol (1) (Control) and hair treated with Protocol (2) (6 treatments), and a lower Young's modulus than hair treated according to Protocol (1) (Control), which was particularly suprising. This suggests further hydration of the fiber leading to plasticization. The improved durability, hydration, and moisturization exhibited by the hair treated according to Protocol (2) (6 treatments) and Protocol (3) (6 treatments and cleanse) is significant and surprising.

Definitions

The term "hair" as used herein includes hair of the head, beard hair, mustache hair, eyebrow hair, eyelashes, and body hair, unless otherwise specified.

As used herein, the terms "comprising," "having," and "including" are used in their open, non-limiting sense.

The term "oil" means any fatty substance that is in liquid form at room temperature (25° C.) and at atmospheric pressure.

The term "solid fatty compound" is a fatty compound that is not an oil, i.e., any fatty substance that is a solid at room temperature (25° C.) and at atmospheric pressure.

The term "hydrocarbon-based oil" is interchangeable with the term "hydrocarbon oil" means an oil mainly containing hydrogen and carbon atoms.

The term "silicone-based oil" is interchangeable with the term "silicone oil" and the term "oganosiloxane oil" and is an oil containing silicone atoms, especially oils having Si—O groups.

The term "fluoro oil" means an oil comprising at least one fluorine atom.

The oils may optionally comprise oxygen, nitrogen, sulphur and/or phosphorus atoms, for example in the form of hydroxyl or acid radicals.

For the purposes of the present invention, the term "volatile oil" means an oil (or non-aqueous medium) capable of evaporating on contact with the skin in less than one hour, at room temperature and at atmospheric pressure. The volatile oil is a volatile cosmetic oil, which is liquid at room temperature, especially having a non-zero vapour pressure, at room temperature and atmospheric pressure, in particular having a vapour pressure ranging from 0.13 Pa to 40 000 Pa (10-3 to 300 mmHg), preferably ranging from 1.3 Pa to 13 000 Pa (0.01 to 100 mmHg), and preferentially ranging from 1.3 Pa to 1300 Pa (0.01 to 10 mmHg).

For the purposes of the present disclosure, the term "non-volatile oil" means an oil with a vapour pressure of less than 0.13 Pa.

The term "silicone emulsifier" is interchangeable with the term "silicone-based emulsifier" and the term "oganosiloxane emulsifier" and refers to an emulsifier containing one or more silicone atoms.

The term "non-silicone emulsifier" is interchangeable with the term "non-silicone-based emulsifier" and refers to an emulsifiers that does not contain silicone atoms.

The term "rinse-off" as used herein indicates that the composition is used in a context whereby the composition is intended to be rinsed or washed from a treated surface, (e.g. skin, hair, or hard surfaces) either after or during the application of the product. These rinse-off compositions are to be distinguished from compositions referred to a "leave-on" compositions. For example, a rinse-off composition is applied to the hair, optionally allowed to remain on the hair for a short time (e.g., a few second up to about 5, 10, or 15 minutes) and subsequently rinsed from the hair before the hair styled.

A "leave-on" (also called leave-in) composition refers to a composition that is applied to hair and is not subjected to immediate rinsing and/or washing, for example for at least 4 hours or for a period of time ranging from 4 hours up to 72 hours, from 4 hours up to 48 hours, or from 8 hours up to 36 hours, or from 8 hours up to 24 hours. In other words, the product is applied to the hair and remains on the hair, as styled, i.e., it is not removed from the hair prior to styling the hair.

For purposes of the instant disclosure the term "nonionic emulsifier" is interchangeable with the term "nonionic surfactant." Reference to a nonionic emulsifier (or nonionic surfactant) in the leave-on hair treatment compositions of the instant disclosure does not indicate that the composition is an emulsion. In various embodiments, the leave-on hair treatment composition is an emulsion but in various embodiments, the leave on hair-treatment composition is not an emulsion.

The leave-on hair treatment composition of the instant disclosure may be in the form of an emulsion, for example, a microemulsion, a water-in-oil emulsion, an oil-in-water emulsion, a micellar emulsion, or a bicontinuous emulsion, but it is not necessarily in the form of an emulsion. In a preferred embodiment, the leave-on hair treatment composition is a microemulsion. In a preferred embodiment, the leave-on hair treatment composition is a bicontinous emulsion, preferably a bicontinous microemulsion.

The term "transparent" with respect to a transparent composition indicates that the composition has transmittance of at least 80% at a wavelength of 600 nm, for example measured using a Lambda 40 UV-visible spectrometer. The compositions may have, for example, a transmittance of at least 80%, at least 90%, or at least 95% at a wavelength of 600 nm, measured, for example, using a Lambda 40 UV-visible spectrometer. The term "clear" is interchangeable with the term "transparent" for purposes of the instant disclosure. A human can typically see through a transparent composition, for example, and read the text on the other side of a clear glass or clear plastic bottle containing the composition.

The term "translucent" with respect to a translucent composition indicates that the composition has a transmittance of at least 50% at a wavelength of 600 nm, for example measured using a Lambda 40 UV-visible spectrometer. A human cannot likely see through a translucent composition, for example, and read the text on the other side of a clear glass or clear plastic bottle containing the composition. Rather, the text is usually blurred and difficult or not possible to read, yet movement and structure can normally be identified.

An "opaque" composition is a composition that is not transparent or translucent.

In the context of the instant disclosure, a "composition colorant" is a compound that colors the composition but does not have an appreciable coloring effect on hair. In other words, the composition colorant is included to provide a coloring to the composition for aesthetic appeal, which is not intended to impart coloring properties to hair. Styling gels, for example, can be found in a variety of different colors (e.g., light blue, light pink, etc.) yet application of the styling gel to the hair does not change the color of the hair.

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The expression "one or more" means "at least one" and thus includes individual components as well as mixtures/combinations.

Other than in the operating examples, or where otherwise indicated, all numbers expressing quantities of ingredients and/or reaction conditions may be modified in all instances by the term "about," meaning within +/−5% of the indicated number.

Some of the various categories of components identified may overlap. In such cases where overlap may exist and the composition includes both components (or the composition includes more than two components that overlap), an overlapping compound does not represent more than one component. For example, a fatty acid may be considered both an emulsifier and a fatty compound. If a particular composition includes both an emulsifier and a fatty compound, a single fatty acid will serve as only the emulsifier or only the fatty compound (the single fatty acid does not serve as both the emulsifier and the fatty component).

The salts referred to throughout the disclosure may include salts having a counter-ion such as an alkali metal, alkaline earth metal, or ammonium counter-ion. This list of counter-ions, however, is non-limiting.

The term "treat" (and its grammatical variations) as used herein refers to the application of the compositions of the present disclosure onto the surface of keratinous substrates such as hair.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc.

All components positively set forth throughout the instant disclosure may be negatively excluded from the claims, e.g., a claimed composition may be "free," "essentially free" (or "substantially free") of one or more components that are positively set forth in the instant disclosure. As an example, silicones can optionally be included in the compositions but preferably the compositions are free or essentially free from silicones. Silicones are synthetic polymers made up of repeating units of siloxane, elemental silicon and oxygen, combined with other elements, most often carbon and hydrogen. Thus, silicones are also called polysiloxanes.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of alkoxylated compounds, for example, ethoxylated thickeners and/or ethoxylated surfactants. Likewise, a particular composition may be free or essentially free of sulfates, such as sulfate surfactants.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The compositions described throughout this disclosure may be a "leave-on" composition. A "leave-on" (also called leave-in) composition refers to a composition that is applied to skin or hair and is not subjected to immediate rinsing and/or washing, for example for at least 4 hours or for a period of time ranging from 4 hours up to 72 hours, from 4 hours up to 48 hours, or from 8 hours up to 36 hours, or from 8 hours up to 24 hours. In other words, the product is applied to the hair and remains on the hair, as styled, i.e., it is not removed from the hair prior to styling the hair.

The invention claimed is:

1. A leave-on hair treatment composition comprising:
   (a) about 5 to about 30 wt. % of water;
   (b) about 10 to about 40 wt. % of one or more polyols chosen from glycerin, ethylene glycol, propylene glycol, butylene glycol, hexylene glycol, pentylene glycol, diethylene glycol, dipropylene glycol, and 1,3 propanediol;
   (c) about 35 to about 75 wt. % of one or more oils, wherein the one or more oils comprise:
      (c)(i) about 30 to about 60 wt. % of one or more hydrocarbon oils chosen from isododecane, $C_3$-$C_{14}$ isoalkanes, and combinations thereof; and
      (c)(ii) about 5 to about 20 wt. % of one or more silicone oils; and
   (d) at least 0.5% to about 5 wt. % of one or more C1-C9 non-polymeric and non-thiol, mono-, di-, and/or tri-carboxylic acids, and/or a salt thereof, or a combination thereof;
   wherein the ratio of ((a)+(b)) to (c) is 1:1 to 1:5; and
   all percentages by weight are relative to a total weight of the composition.

2. The composition of claim 1 comprising about 5 to about 25 wt. % of the water.

3. The composition of claim 1 comprising about 35 to about 70 wt. % of the one or more oils.

4. The composition of claim 1, wherein the one or more C1-C9 non-polymeric and non-thiol, mono-, di-, and/or tri-carboxylic acids is selected from formic acid, acetic acid, lactic acid, propionic acid, butyric acid, gluconic acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, and arachidic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, and 2,6-naphthalene dicarboxylic acid, citric acid, isocitric acid, aconitic acid, propane-1,2,3-tricarboxylic acid, and benzene-1,3,5-tricarboxylic acid, a salt thereof, and a combination thereof.

5. The composition of claim 1 being translucent or transparent.

6. The composition of claim 1 having a pH of about 3 to about 6.

7. The composition of claim 1, further comprising:
(e) one or more emulsifiers.

8. The composition of claim 7, wherein at least one of the one or more emulsifiers is a silicone emulsifier.

9. The composition of claim 7, wherein at least one of the one or more emulsifiers is a non-silicone emulsifier.

10. The composition of claim 1, further comprising:
(f) one or more C1-C6 monoalcohols.

11. The composition of claim 1, further comprising:
(g) one or more thickening agents.

12. The composition of claim 11, wherein the one or more thickening agents is selected from polyacrylate crosspolymers, cationic acrylate copolymers, anionic acrylic or carboxylic acid polymers, polyacrylamide polymers, polysaccharides, gums, polyquaterniums, vinylpyrrolidone homopolymers/copolymers, C8-24 hydroxyl substituted aliphatic acid, C8-24 conjugated aliphatic acid, sugar fatty esters, polyglyceryl esters, and a combination thereof.

13. The composition of claim 1, further comprising:
(h) one or more humectants.

14. The composition of claim 13, wherein at least one of the one or more humectants is a hydroxyalkyl urea.

15. The composition of claim 14, wherein the hydroxyalkyl urea is selected from N-(2-hydroxyethyl) urea, N-(2-hydroxypropyl) urea, N-(3-hydroxypropyl) urea, N-(2,3-dihydroxypropyl) urea, N-(2,3,4,5,6-pentahydroxyhexyl) urea, N-methyl-N-(1,3,4,5,6-pentahydroxy-2-hexyl) urea, N-methyl-N'-(1-hydroxy-2-methyl-2-propyl) urea, N-(1-hydroxy-2-methyl-2-propyl) urea, N-(1,3-dihydroxy-2-propyl) urea; N-(trishydroxymethylmethyl) urea, N-ethyl-N'-(2-hydroxyethyl) urea, N,N-bis-(2-hydroxy-ethyl) urea, N,N'-bis-(2-hydroxyethyl) urea, N,N-bis-(2-hydroxypropyl) urea, N,N'-bis-(2-hydroxypropyl) urea, N,N-bis-(2-hydroxyethyl)-N'-propyl urea, N,N-bis-(2-hydroxypropyl)-N'-(2-hydroxyethyl) urea, N-tert-butyl-N'-(2-hydroxyethyl)-N'-(2-hydroxypropyl) urea, N-(1,3-dihydroxy-2-propyl)-N'-(2-hydroxyethyl) urea, N,N-bis-(2-hydroxyethyl)-N',N'-dimethyl urea, N,N,N',N'-tetrakis-(2-hydroxyethyl) urea, and N',N'-bis-(2-hydroxyethyl)-N',N'-bis-(2-hydroxypropyl) urea.

16. A leave-on hair treatment composition comprising:
(a) about 5 to about 30 wt. % of water;
(b) about 10 to about 40 wt. % of one or more polyols chosen from glycerin, ethylene glycol, propylene glycol, butylene glycol, hexylene glycol, pentylene glycol, diethylene glycol, dipropylene glycol, and 1,3 propanediol;
(c) about 35 to about 75 wt. % of one or more oils, wherein the one or more oils comprise:
(c)(i) about 30 to about 60 wt. % of one or more hydrocarbon oils chosen from isododecane, $C_{13}$-$C_{14}$ isoalkanes, and combinations thereof; and
(c)(ii) about 5 to about 20 wt. % of one or more silicone oils;
(d) at least 0.5% to about 5 wt. % of one or more C1-C9 non-polymeric and non-thiol, mono-, di-, and/or tri-carboxylic acids, a salt thereof, or a combination thereof;
(e) about 1 to about 6 wt. % of one or more emulsifiers, wherein at least one of the one or more emulsifiers is a silicone emulsifier;
(f) about 0.1 to about 5 wt. % of one or more thickening agents;
(g) optionally, up to about 5 wt. % of one or more humectants; and
(h) optionally, up to about 5 wt. % of one or more additional ingredients;
wherein the ratio of ((a)+(b)) to (c) is 1:1 to 1:5;
the composition is translucent or transparent; and
the composition has a pH of about 3 to about 6;
all percentages by weight are relative to a total weight of the composition.

17. The composition of claim 16, wherein the composition comprises one or more humectants selected from hydroxyalkyl ureas.

18. A method for treating hair comprising applying the leave-on hair treatment composition of claim 1 to the hair and styling the hair without first rinsing the composition from the hair.

19. The composition of claim 1 comprising about 5 to about 25 wt. % of the water and about 35 to about 70 wt. % of the one or more oils.

* * * * *